United States Patent
Hall-Goulle et al.

(10) Patent No.: US 6,551,761 B1
(45) Date of Patent: Apr. 22, 2003

(54) PHOTOACTIVATABLE NITROGEN-CONTAINING BASES BASED ON α-AMMONIUM KETONES, IMINIUM KETONES OR AMIDINIUM KETONES AND ARYL BORATES

(75) Inventors: Véronique Hall-Goulle, Reinach (CH); Sean Colm Turner, Evanston, IL (US); Allan Francis Cunningham, Somers, NY (US)

(73) Assignee: Ciba Specialty Chemical Corporation, Tarrytown, NY (US)

( * ) Notice: Subject to any disclaimer, the term of this patent is extended or adjusted under 35 U.S.C. 154(b) by 86 days.

(21) Appl. No.: 09/657,090

(22) Filed: Sep. 7, 2000

Related U.S. Application Data

(63) Continuation-in-part of application No. 09/028,985, filed on Feb. 25, 1998, now abandoned.

(30) Foreign Application Priority Data

Feb. 26, 1997 (CH) ................................ 0444/97

(51) Int. Cl.[7] .................. C07D 487/04; G03F 7/004
(52) U.S. Cl. .................. 430/284.1; 522/31; 522/39; 540/500; 544/229; 544/263; 544/349; 564/183; 564/194; 430/914; 430/919; 430/920; 430/923; 430/280.1; 430/281.1
(58) Field of Search ................ 544/229, 263, 544/349; 564/183, 194; 540/500; 522/31, 39; 430/284.1

(56) References Cited

U.S. PATENT DOCUMENTS 5,077,402 A    12/1991    Desobry et al. .............. 544/87

FOREIGN PATENT DOCUMENTS

EP    284561    3/1988
EP    0377321   7/1990

OTHER PUBLICATIONS

Chem. Ber. 94, (1961), pp. 3147–3150.
Patent Abstract of Japan 09241614.
Derwent Abstr. 98–126164.
Derwent Abstr. 98–114813.
Derwent Abstr. 98–082667.
Patent Abstr. of Japan 09227854.
Patent Abstr. of Japan 09263063.
Patent Abstr. of Japan 07070068.
Patent Abstr. of Japan 07070221.
Derwent Abstr. 98–105135.
J. Org. Chem. USSR 23(4), (1987), pp. 792–796.
Chem. Abstr. vol. 75, No. 12, (1971), 80214j.
J. Polymer Mater. Science, Eng. (1992) 66, pp. 237–238.
Journal of Polymer Science. Chem. Ed. vol. 12, pp. 2943–2951 (1974).
Journal Chemical Society © 1971, pp. 1863–1869.
Chemical Material 1996, 8, pp. 1360–1362.

*Primary Examiner*—Cynthia Hamilton
(74) *Attorney, Agent, or Firm*—Tyler A. Stevenson; David R. Crichton

(57) ABSTRACT

This invention relates to α-ammonium ketones, iminium ketones or amidinium ketones in the form of their tetraaryl- or triarylalkylborate salts which can be photochemically converted into amines, imines or amidines as well as to a process for their preparation. This invention also relates to base-polymerisable or crosslinkable compositions comprising these α-ammonium ketones, iminium ketones or amidinium ketones in the form of their tetra- or triarylalkylborate salts, to a process for carrying out photochemically induced, base-catalysed reactions as well as to their use as photoinitiators for base-catalysed reactions.

18 Claims, No Drawings

PHOTOACTIVATABLE NITROGEN-CONTAINING BASES BASED ON α-AMMONIUM KETONES, IMINIUM KETONES OR AMIDINIUM KETONES AND ARYL BORATES

This is a continuation-in-part of application Ser. No. 09/028,985, filed Feb. 25, 1998 now abandoned.

The present invention relates to α-ammonium ketones, iminium ketones or amidinium ketones in the form of their tetraaryl- or triarylalkylborate salts which can be photochemically converted into amines, imines or amidines as well as to a process for their preparation. This invention also relates to base-polymerisable or crosslinkable compositions comprising these α-ammonium ketones, iminium ketones or amidinium ketones in the form of their tetra- or triarylalkylborate salts, to a process for carrying out photochemically induced, base-catalysed reactions as well as to their use as photoinitiators for base-catalysed reactions.

The photolytic cleavage of specific α-amino ketones into radicals and the photopolymerisation of olefinically unsaturated monomers or oligomers which this initiates have long been known and are described, for example, in EP-A-284 561.

In addition to radically polymerisable oligomers or monomers, base-catalysable systems have been disclosed in particular for photolithographic processes. These systems require a photoinitiator which releases a base on exposure to light. D. R. MacKean et al., Polym. Mater. Sci. Eng. (1992), 66, 237–238, for example, report on the photostructuring of polyimide using specific carbamates as photoinitiators.

In J. of Polymer Science: Polym. Chem. Ed., Vol. 12, 2943–2951 (1974), Ko et al. report on $BF_4^-$ salts containing α-ammonium ketones which on exposure to light decompose into radicals with α- cleavage but which do not form any free amine and which are therefore unsuitable as latent bases.

J. Chem. Soc. (C), 1971, 1863–1869 describes bromine salts of α-ammonium ketones which on exposure to light result in protonated amines and which are therefore also unsuitable as latent bases.

In Chem. Mater. 1996, 8, 1360–1362, Neckers et al. recently reported on novel systems for photostructuring based on polymeric ammonium phenylborates containing mobile benzophenone groups at the polymer structure.

Surprisingly, it has now been found that certain α-ammonium ketones, iminium ketones or amidinium ketones in the form of their tetraaryl- or triarylalkylborate salts release an amine, imine or amidine group on exposure to visible light or UV light. These groups are sufficiently basic to initiate a large number of base-catalysable reactions, in particular polymerisation reactions. These compounds are of high sensitivity and through the choice of the substitution pattern the absorption spectrum can be varied within a wide range.

These compounds make it possible to prepare so-called one-pot systems with base-catalysable oligomers or monomers having an extremely long storage life. A polymerisation reaction, for example, is initiated only after exposure to light. The systems can be formulated with little or no solvent, since the compounds can be dissolved in the monomers or oligomers without being affected. The active catalyst is formed only after exposure to light. These systems can be employed for numerous purposes, such as for finishes, coatings, moulding compounds or photolithographic reproductions.

This invention provides compounds of formula (I)

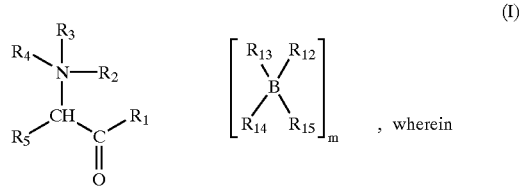

m is 1 or 2 and corresponds to the number of positive charges of the cation;

$R_1$ is phenyl, naphthyl, phenanthryl, anthracyl, pyrenyl, 5,6,7,8-tetrahydro-2-naphthyl, 5,6,7,8-tetrahydro-1-naphthyl, thienyl, benzo[b]thienyl, naphtho[2,3-b]thienyl, thianthrenyl dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyi, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, terphenyl, stilbenyl, fluorenyl or phenoxazinyl, these radicals being unsubstituted or mono- or polysubstituted by $C_1-C_{18}$alkyl, $C_3-C_{18}$alkenyl, $C_3-C_{18}$alkynyl, $C_1-C_{18}$haloalkyl, $NO_2$, $NR_6R_7$, $N_3$, OH, CN, $OR_8$, $SR_8$, $C(O)R_9$, $C(O)OR_{10}$ or halogen, or $R_1$ is a radical of formula A or B

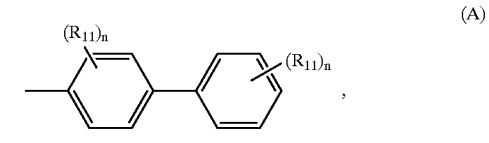

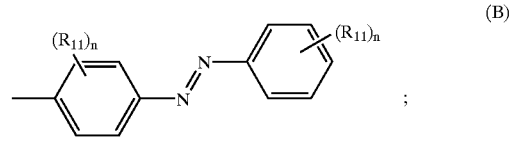

$R_2$, $R_3$ and $R_4$ are each independently of one another hydrogen, $C_1-C_{18}$alkyl, $C_3-C_{18}$alkenyl, $C_3-C_{18}$alkynyl or phenyl, or $R_2$ and $R_3$ and/or $R_4$ and $R_3$ form each independently of one another a $C_2-C_{12}$alkylene bridge; or $R_2$, $R_3$, $R_4$, together with the linking nitrogen atom, are a phosphazene base of the $P_1$, $P_2$, P <t/4> type or a group of the structural formula (a), (b), (c), (d), (e), (f) or (g)

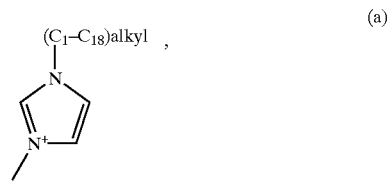

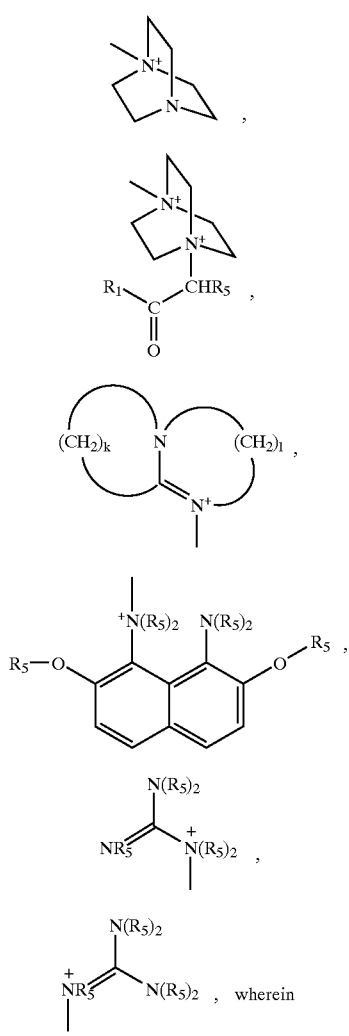

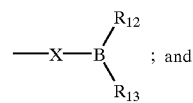

X is C$_1$–C$_{20}$alkylene, C$_2$–C$_{20}$alkylene which is interrupted by —O—, —S— or NR$_8$, or X is

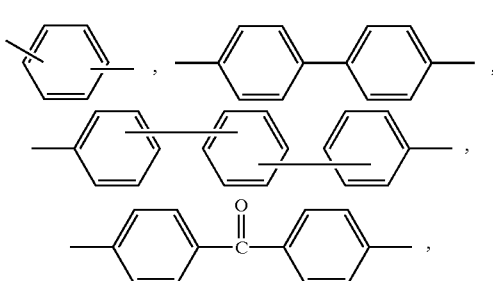

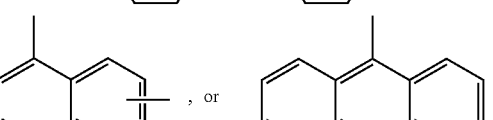

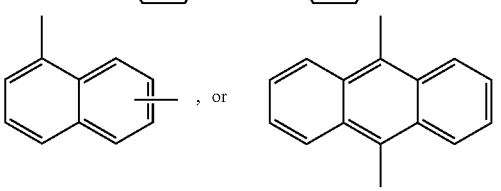

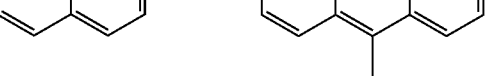

k and l are each independently of the other a number from 2 to 12;

R$_5$, R$_6$, R$_7$, R$_8$, R$_9$ and R$_{10}$ are hydrogen or C$_1$–C$_{18}$alkyl; or R$_5$ and R$_1$, together with the linking carbon atoms, are a benzocyclopentanone radical;

R$_{11}$ is C$_1$–C$_{18}$alkyl, C$_2$–C$_{18}$alkenyl, C$_2$–C$_{18}$alkynyl, C$_1$–C$_{18}$haloalkyl, NO$_2$, NR$_6$R$_7$, OH, CN, OR$_8$, SR$_8$, C(O)R$_9$, C(O)OR$_{10}$ or halogen; and n is 0 or 1, 2 or 3;

R$_{12}$, R$_{13}$ and R$_{14}$ is phenyl or another aromatic hydrocarbon, these radicals being unsubstituted or mono- or polysubstituted by C$_1$–C$_{18}$alkyl, C$_3$–C$_{18}$alkenyl, C$_3$–C$_{18}$alkynyl, C$_1$–C$_{18}$haloalkyl, NO$_2$, OH, CN, OR$_8$, SR$_8$, C(O)R$_9$, C(O)OR$_{10}$ or halogen;

R$_{15}$ is C$_1$–C$_{18}$alkyl, phenyl or another aromatic hydrocarbon, the radicals phenyl and aromatic hydrocarbon being unsubstituted or mono- or polysubstituted by C$_1$–C$_{18}$alkyl, C$_3$–C$_{18}$alkenyl, C$_3$–C$_{18}$alkynyl, C$_1$–C$_{18}$haloalkyl, NO$_2$, OH, CN, OR$_8$, SR$_8$, C(O)R$_9$, C(O)OR$_{10}$ or halogen, R$_{15}$ is a radical The absorption maximum can be varied within a wide range through the choice of the aromatic or heteroaromatic R$_1$ and of the respective borate anion, and so the photosensitivity of the compounds can be shifted from the UV into the daylight region.

Alkyl in the various radicals having up to 18 carbon atoms is a branched or unbranched radical such as methyl, ethyl, propyl, isopropyl, n-butyl, secbutyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl octadecyl. Preference is given to alkyl having 1 to 12, especially 1 to 6, carbon atoms.

Alkenyl having 3 to 18 carbon atoms is a branched or unbranched radical such as propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl or n-4-octadecenyl. Preference is given to alkenyl having 3 to 12, especially 3 to 6, carbon atoms.

Alkynyl having 3 to 18 carbon atoms is a branched or unbranched radical such as propynyl (—CH$_2$—C≡CH), 2-butynyl, 3-butynyl, n-2-octynyl, or n-2-octadecynyl. Preference is given to alkynyl having 3 to 12, especially 3 to 6, carbon atoms.

The C$_2$–C$_{12}$alkylene bridge is ethylene, propylene, butylene, pentylene, hexylene, heptylene, octylene, nonylene, decylene, undecylene or dodecylene.

Halogen is fluoro, chloro, bromo or iodo.

Typical examples of C$_1$–C$_{18}$haloalkyl are fully or partly halogenated C$_1$–C$_{18}$alkyl. Illustrative example thereof are the positional isomers of mono- to decafluoropentyl, mono- to octafluorobutyl, mono- to hexafluoropropyl, mono- to tetrafluoroethyl and mono- and difluoromethyl and also the corresponding chloro, bromo and iodo compounds. Preference is given to the perfluorinated alkyl radicals. Examples of these are perfluoropentyl, perfluorobutyl, perfluoropropyl, perfluoroethyl and, in particular, trifluoromethyl.

Examples of the $NR_8R_9$ amino group are the respective monoalkyl or dialkylamino groups such as methylamino, ethylamino, propylamino, butylamino, pentylamino, hexylamino, octadecylamino, dimethylamino, diethylamino, dipropylamino, diisopropylamino, di-n-butylamino, di-isobutylamino, dipentylamino, dihexylamino or dioctadecylamino. Further dialkylamino groups are those in which the two radicals independently of one another are branched or unbranched, for example methylethylamino, methyl-n-propylamino, methylisopropylamino, methyl-n-butylamino, methylisobutylamino, ethylisopropylamino, ethyl-n-butylamino, ethylsobutylamino, ethyl-tert-butylamino, isopropyl-n-butylamino or isopropylisobutylamino.

The alkoxy group $OR_{10}$ having up to 18 carbon atoms is a branched or unbranched radical such as methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. Preference is given to alkoxy having 1 to 12, especially 1 to 8, for example 1 to 6, carbon atoms.

Examples of the thioalkyl group $SR_{10}$ are thiomethyl, thioethyl, thiopropyl, thiobutyl, thiopentyl, thiohexyl, thioheptyl, thiooctyl or thiooctadecyl, it being possible for the alkyl radicals to be linear or branched.

Aromatic hydrocarbons, such as may be present in the novel compounds ($R_{13}$, $R_{14}$ or $R_{15}$), can contain, for example, one or several, preferably 1 or 2, hetero atoms. Suitable hetero atoms are, for example, N, O, P or S, preferably N or O. Typical examples of aromatic hydrocarbons are: phenyl, α- and β-naphthyl, stilbenyl, biphenyl, o-, m-, p-terphenyl, triphenylphenyl, binaphthyl, anthracyl, phenanthryl, pyrenyl, furan-2-yl or furan-3-yl, thiophen-2-yl or thiophen-3-yl, pyridin-2-yl, pyridin-3-yl or pyridin-4-yl, quinolyl or isoquinolyl.

Examples of $R_1$ are phenyl, naphthyl, phenanthryl, anthracyl, pyrenyl, 5,6,7,8-tetrahydro-2-naphthyl, 5,6,7,8-tetrahydro-1-naphthyl, thienyl, benzo[b]thienyl, naphtho[2,3-b]thienyl, thianthrenyl, dibenzofuryl, chromenyl, xanthenyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cimolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, stilbenyl, tephenyl, fluorenyl, phenoxazinyl, methoxyphenyl, 2,4-dimethoxyphenyl, 2,4,6-trimethoxyphenyl, bromophenyl, tolyl, xylyl, mesityl, nitrophenyl, dimethylaminophenyl, diethylaminophenyl, aminophenyl, diaminophenyl, 1-naphthyl, 2-naphthyl, 1-phenylamino-4-naphthyl, 1-methylnaphthyl, 2-methylnaphthyl, 1-methoxy-2-naphthyl, 2-methoxy-1-naphthyl, 1-dimethylamino-2-naphthyl, 1,2-dimethyl-4-naphthyl, 1,2-dimethyl-6-naphthyl, 1,2-dimethyl-7-naphthyl, 1,3-dimethyl-6-naphthyl, 1,4-dimethyl-6-naphthyl, 1,5-dimethyl-2-naphthyl, 1,6-dimethyl-2-naphthyl, 1-hydroxy-2-naphthyl, 2-hydroxy-1-naphthyl, 1,4-dihydroxy-2-naphthyl, 7-phenanthryl, 1-anthryl, 2-anthryl, 9-anthryl, 3-benzo[b]thienyl, 5-benzo[b]thienyl, 2-benzo[b]thienyl, 4-dibenzofuryl, 4,7-dibenzofuryl, 4-methyl-7-dibenzofuryl, 2-xanthenyl, 8-methyl-2-xanthenyl, 3-xanthenyl, 2-phenoxathiinyl, 2,7-phenoxathiinyl, 2-pyrrolyl, 3-pyrrolyl, 5-methyl-3-pyrrolyl, 2-imidazolyl, 4-imidazolyl, 5-imidazolyl, 2-methyl-4-imidazolyl, 2-ethyl-4-imidazolyl, 2-ethyl-5-imidazolyl, 3-pyrazolyl, 1-methyl-3-pyrazolyl, 1-propyl-4-pyrazolyl, 2-pyrazinyl, 5,6-dimethyl-2-pyrazinyl, 2-indolizinyl, 2-methyl-3-isoindolyl, 2-methyl-1-isoindolyl, 1-methyl-2-indolyl, 1-methyl-3-indolyl, 1,5-dimethyl-2-indolyl, 1-methyl-3-indazolyl, 2,7-dimethyl-8-purinyl, 2-methoxy-7-methyl-8-purinyl, 2-quinolizinyl, 3-isoquinolyl, 6-isoquinolyl, 7-isoquinolyl, isoquinolyl, 3-methoxy-6-isoquinolyl, 2-quinolyl, 6-quinolyl, 7-quinolyl, 2-methoxy-3-quinolyl, 2-methoxy-6-quinolyl, 6-phthalazinyl, 7-phthalazinyl, 1-methoxy-6-phthalazinyl, 1,4-dimethoxy-6-phthalazinyl, 1,8-naphthyridin-2-yl, 2-quinoxalinyl, 6-quinoxalinyl, 2,3-dimethyl-6-quinoxalinyl, 2,3-dimethoxy-6-quinoxalinyl, 2-quinazolinyl, 7-quinazolinyl, 2-dimethylamino-6-quinazolinyl, 3-cinnolinyl, 6-cinnolinyl, 7-cinnolinyl, 3-methoxy-7-cinnolinyl, 2-pteridinyl, 6-pteridinyl, 7-pteridinyl, 6,7-dimethoxy-2-pteridinyl, 2-carbazolyl, 3-carbazolyl, 9-methyl-2-carbazolyl, 9-methyl-3-carbazolyl, β-carbolin-3-yl, 1-methyl-β-carbolin-3-yl, 1-methyl-β-carbolin-6-yl, 3-phenanthridinyl, 2-acridinyl, 3-acridinyl, 2-perimidinyl, 1-methyl-5-perimidinyl, 5-phenanthrolinyl, 6-phenanthrolinyl, 1-phenazinyl, 2-phenazinyl, 3-isothiazolyl, 4-isothiazolyl, 5-isothiazolyl, 2-phenothiazinyl, 3-phenothiazinyl, 10-methyl-3-phenothiazinyl, 3-isoxazolyl, 4-isoxazolyl, 5-isoxazolyl, 4-methyl-3-furazanyl, 2-phenoxazinyl or 10-methyl-2-phenoxazinyl.

Where $R_1$ and $R_5$, together with the linking carbon atoms, form a benzocyclopentanone radical, this means structures as follows

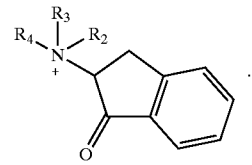

Typical examples of phosphazene bases of the $P_1$, $P_2$ or P <t/4> type are

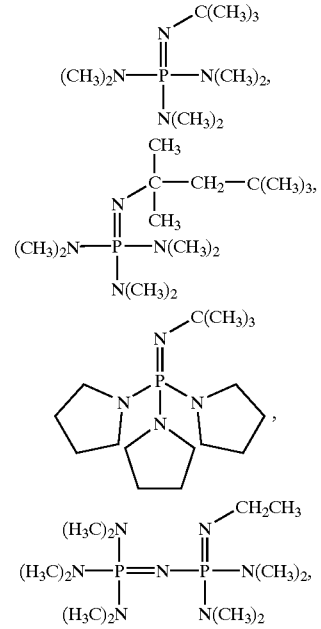

-continued

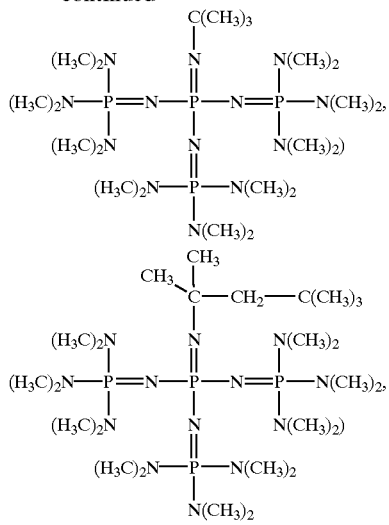

where the phosphazene bases can be bound via the nitrogen imine as well as via one of the tertiary nitrogen atoms to the $CH_2$ group of the ketone.

The phosphazene bases are preferably bound via one of the tertiary nitrogen atoms to the $CH_2$ group of the ketone.

$R_1$ is preferably phenyl, naphthyl, phenanthryl, anthracyl, pyrenyl, 5,6,7,8-tetrahydro-2-naphthyl, 5,6,7,8-tetrahydro-1-naphthyl, thienyl, benzo[b]thienyl, naphto[2,3-b]thienyl, thianthrenyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phtalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, terphenyl, stilbenyl, fluorenyl or phenoxazinyl, these radicals being unsubstituted or mono- or polysubstituted by $C_1$–$C_{18}$alkyl, $C_3$–$C_{18}$alkenyl, $C_3$–$C_{18}$alkynyl, $C_1$–$C_{18}$haloalkyl, $NO_2$, $NR_6R_7$, $N_3$, OH, CN, $OR_8$, $SR_8$, $C(O)R_9$, $C(O)OR_{10}$ or halogen; or $R_1$ is a radical of formula A or B

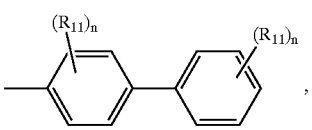

(A)

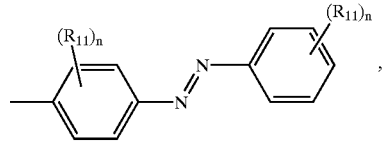

(B)

or $R_1$ and $R_5$, together with the linking carbon atoms, are a benzocyclopentanone radical.

$R_1$ is particularly preferably phenyl, naphthyl, pyrenyl, thioxanthyl or phenothiazinyl, these radicals being unsubstituted or mono- or polysubstituted by $C_1$–$C_{18}$alkyl, $C_1$–$C_{18}$haloalkyl, $NR_6R_7$, CN, $NO_2$, $SR_8$ or $OR_8$.

$R_2$, $R_3$ and $R_4$ are preferably each independently of one another hydrogen, $C_1$–$C_{18}$alkyl, or $R_2$ and $R_3$, and/or $R_4$ and $R_3$ form each independently of one another a $C_2$–$C_{12}$alkylene bridge; or $R_2$, $R_3$, $R_4$, together with the linking nitrogen atom, are a group of the structural formulae (a), (b), (c), (d), (e), (f), (g), as indicated above, or a phosphazene base of the $P_1$, $P_2$ or P <t/4> type.

k and l are each independently of the other a number from 2 to 12, preferably a number from 2 to 6.

Particularly preferred compounds are those, wherein $R_2$, $R_3$ and $R_4$ are each independently of one another $C_1$–$C_{18}$alkyl, or $R_2$, $R_3$, $R_4$, together with the nitrogen atom, form a group of the structural formula (a), (b), (c), (d) or (e), as indicated above.

$R_{12}$, $R_{13}$, $R_{14}$ are preferably phenyl, biphenyl, naphthyl, anthracyl or phenanthryl, these radicals being unsubstituted or mono- or polysubstituted by $C_1$–$C_{18}$alkyl, $C_1$–$C_{18}$haloalkyl, $NO_2$, OH, CN, $OR_8$, or halogen, and $R_{15}$ is $C_1$–$C_{18}$alkyl or phenyl which is unsubstituted or mono- or polysubstituted $C_1$–$C_{18}$alkyl, $C_1$–$C_{18}$haloalkyl, $NO_2$, OH, CN, $OR_8$ or halogen.

Suitable borate anions for the nitrogenous base cation in the compounds of formula I are also to be found, inter alia, in U.S. Pat. No. 4,772,530, GB 2307474, GB 2307473, GB 2307472, EP 775706. Illustrative examples are triphenylbutylborate, triphenylhexylborate, triphenylmethylborate, dimesitylphenylmethylborate or dimesitylphenylbutylborate, di(bromomesityl) phenylmethylborate or di(bromomesityl)phenylbutylborate, tris(3-fluorophenyl)hexylborate, tris(3-fluorophenyl) methylborate or tris(3-fluorophenyl)butylborate, dichloromesitylphenylmethylborate or dichloromesitylphenylbutylborate, tris(dichloromesityl) methylborate, tris(3-chlorophenyl)hexylborate, tris(3-chlorophenyl)methylborate or tris(3-chlorophenyl) butylborate, tris(3-bromophenyl)hexylborate, tris(3-bromphenyl)methylborate or tris(3-bromophenyl) butylborate, tris(3,5-difluorophenyl)hexylborate, dimesitylbiphenylbutylborate, dimesitylnaphthylmethylborate or dimesitylnaphthylbutylborate, di(o-tolyl)-9-anthracylmethylborate or di(o-tolyl)-9-anthracylbutylborate, dimesityl-9-phenanthrylphenylborate or dimesityl-9-phenanthrylphenylbutylborate or

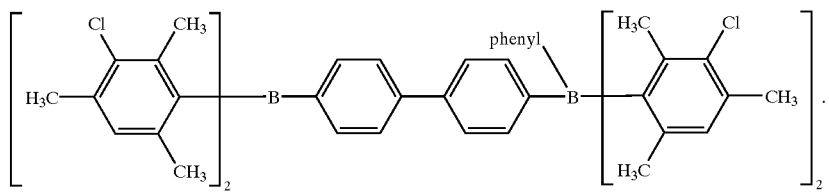

The preparation of these anions is described in the above-mentioned publications.

The preparation of the bromides or iodides of the novel compounds of formula I is carried out, for example, by the methods described by A. Padwa, W. Eisenhardt, R. Gruber and D. Pashayan in J. Am. Chem. Soc., 93, 6998 (1971) or by T. Laird and H. Williams, J. Chem. Soc. (C), 3467 (1971).

The borates are obtained therefrom in analogous manner. The reaction can be carried out in per se known manner. It is useful to also use a solvent or a mixture of solvents, for example hydrocarbons (benzene, toluene, xylene), halogenated hydrocarbons (methylene chloride, chloroform, carbon tetrachloride, chlorobenzene), alkanols (methanol, ethanol, 2-methoxyethanol), and ethers (diethyl ether, dibutyl ether, 1,2-dimethoxyethane), or mixtures thereof.

The reaction Is conveniently carried out in the temperature range from −10° C. to +100° C. It is preferably carried out in the range from 10° C. to 50° C.

This invention also provides a process for the preparation of the compounds of formula I, which comprises reacting in a first step a nitrogenous base of formula II $$NR_2R_3R_4 \quad (II)$$

with an α- halogen ketone of formula III

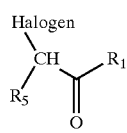

(III)

to a compound of formula IV

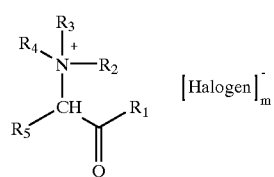

(IV)

and, in a second step, reacting the compounds of formula IV with a compound of formula V

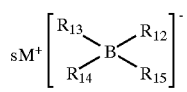

(V)

to the compound of formula I, wherein halogen is bromo or iodo, and M is Na, K or ammonium, and $R_1$, $R_2$, $R_3$, $R_4$, $R_5$, $R_{12}$, $R_{13}$, $R_{14}$ and $R_{15}$ have the meanings and preferred meanings stated above.

This invention also relates to a composition, comprising

A) at least one compound of formula (I), and

B) at least one organic compound which is capable of a base-catalysed addition reaction or substitution reaction.

The base-catalysed addition reaction or substitution reaction can be carried out with low molecular compounds (monomers), with oligomers, with polymeric compounds or with a mixture of these compounds. Examples of reactions which can be carried out both with monomers and with oligomers/polymers using the novel photoinitiators are the Knoevenagel reaction or the Michael addition reaction.

Particularly important compositions are those, wherein component B) is an anionically polymerisable or crosslinkable organic material.

The organic material can be in the form of mono- or polyfunctional monomers, oligomers or polymers.

Particularly preferred oligomeric/polymeric systems are binders or coating systems as are customary in the coatings industry.

Examples of such base-catalysable binders or coating systems are:

a) acrylate copolymers having alkoxysilane or alkoxysiloxane side groups, for example the polymers described in U.S. Pat. No. 4,772,672 or U.S. Pat. No. 4,444,974;

b) two-component systems comprising hydroxyl group-containing polyacrylates, polyesters and/or polyethers and aliphatic or aromatic polyisocyanates;

c) two-component systems comprising functional polyacrylates and a polyepoxide, where the polyacrylate contains carboxyl or anhydride groups;

d) two-component systems comprising fluorine-modified or silicone-modified hydroxyl group-containing polyacrylates, polyesters and/or polyethers and aliphatic or aromatic polyisocyanates;

e) two-component systems comprising (poly)ketimines and aliphatic or aromatic polyisocyanates;

f) two-component systems comprising (poly)ketimines and unsaturated acrylate resins or acetoacetate resins or methyl α-acrylamidomethylglycolate;

h) two-component systems comprising (poly) oxazolidines and polyacrylates containing anhydride groups, or unsaturated acrylate resins or polyisocyanates;

i) two-component systems comprising epoxy-containing polyacrylates and carboxyl-group containing polyacrylates;

l) polymers based on allyl glycidyl ether;

m) two-component systems comprising a (poly)alcohol and a (poly)isocyanate;

n) two-component systems comprising an α,β-ethylenically unsaturated carbonyl compound and a polymer which contains activated $CH_2$ groups, it being possible for the activated $CH_2$ groups to be present either in the main chain or in the side chain or in both, as is described, for example, in EP-B-0 161 697 for (poly)malonate groups. Other compounds having activated $CH_2$ groups are (poly)acetoacetates and (poly) cyanoacetates.

Among these base-catalysable binders particular preference is given to the following:

b) two-component systems comprising hydroxyl group-containing polyacrylates, polyesters and/or polyethers and aliphatic or aromatic polyisocyanates;

c) two-component systems comprising functional polyacrylates and a polyepoxide, where the polyacrylate contains carboxyl or anhydride groups;

i) two-component systems comprising epoxy-containing polyacrylates and carboxyl-group containing polyacrylates;

m) two-component systems comprising a (poly)alcohol and a (poly)isocyanate, and n) two-component systems comprising an α,β-ethylenically unsaturated carbonyl compound and a polymer which contains activated $CH_2$ groups, it being possible for the activated $CH_2$ groups to be present either in the main chain or in the side chain or in both, as is described, for example, in EP-B-0 161 697 for (poly)malonate groups. Other compounds having activated $CH_2$ groups are (poly)acetoacetates and (poly) cyanoacetates.

Two-component systems comprising an α,β-ethylenically unsaturated carbonyl compound and a (poly)malonate, and their preparation, are described in EP-B-0 161 687. The malonate group here can be attached in a polyurethane, polyester, polyacrylate, epoxy resin, polyamide or polyvinyl polymer either in the main chain or in a side chain. The α,β-ethylenically unsaturated carbonyl compound employed can be any double bond activated by a carbonyl group. Examples are esters or amides of acrylic acid or methacrylic acid. In the ester groups it is also possible for additional hydroxyl groups to be present. Diesters and triesters are also possible.

Typical examples are hexanediol diacrylate or trimethylolpropane triacrylate. Instead of the acrylic acid it is also possible to use other acids and their esters or amides, such as crotonic or cinnamic acid.

Under base catalysis, the components of the system react with one another at room temperature to form a crosslinked coating system which is suitable for numerous applications. Owing to its good inherent weathering resistance it is suitable, for example, for exterior applications as well and can, if required, be additionally stabilised by UV absorbers and other light stabilisers.

Other systems suitable as component B) in the novel compositions are epoxy systems. Epoxy resins are suitable for preparing novel, curable mixtures comprising epoxy resins as component B) are those which are customary in epoxy resin technology, examples of such epoxy resins being:

I) Polyglycidyl and poly(β-methylglycidyl)esters, obtainable by reacting a compound having at least two carboxyl groups in the molecule with epichlorohydrin or β-methylepichlorohydrin. The reaction is judiciously carried out in the presence of bases. As the compound having at least two carboxyl groups in the molecule it is possible to use aliphatic polycarboxylic acids. Examples of such polycarboxylic acids are oxalic, succinic, glutaric, adipic, pimelic, suberic, azelaic or dimerised or trimerised linoleic acid. It is also possible, however, to employ cycloaliphatic polycarboxylic acids, such as tetrahydrophthalic, 4-methyltetrahydrophthalic, hexahydrophthalic or 4-methylhexahydrophthalic acid. Aromatic polycarboxylic acids, furthermore, can be used, such as phthalic, isophthalic or terephthalic acid.

II) Polyglycidyl or poly(β-methylglycidyl)ethers, obtainable by reacting a compound having at least two free alcoholic hydroxyl groups and/or phenolic hydroxyl groups with epichlorohydrin or β-methylepichlorohydrin under alkaline conditions or in the presence of an acidic catalyst with subsequent alkali treatment.

The glycidyl ethers of this type are derived, for example, from acyclic alcohols, such as ethylene glycol, diethylene glycol and higher poly(oxyethylene)glycols, propane-1,2-diol or poly(oxypropylene)glycols, propane-1,3-diol, butane-1,4-diol, poly(oxytetramethylene)glycols, pentane-1,5-diol, hexane-1,6-diol, hexane-2,4,6-triol, glycerol, 1,1,1-trimethylolpropane, pentaerythritol, sorbitol, and from polyepichlorohydrins. They also derive, for example, from cycloaliphatic alcohols, such as 1,4-cyclohexanedimethanol, bis(4-hydroxycyclohexyl)-methane or 2,2-bis(4-hydroxycyclohexyl)propane, or possess aromatic nuclei, such as N,N-bis(2-hydroxyethyl)aniline or p,p'-bis(2-hydroxyethylamino)diphenylmethane. The glycidyl ethers can also be derived from mononuclear phenols, such as resorcinol or hydroquinone, or are based on polynuclear phenols, such as bis(4-hydroxyphenyl)methane, 4,4'-dihydroxybiphenyl, bis(4-hydroxyphenyl)sulfone, 1,1,2,2-tetrakis(4-hydroxyphenyl)ethane, 2,2-bis(4-hydroxyphenyl)propane, 2,2-bis(3,5-dibromo-4-hydroxyphenyl)propane and from novolaks, obtainable by condensing aldehydes, such as formaldehyde, acetaldehyde, chloral or furfuraldehyde, with phenols, such as phenol, or with phenols whose nucleus is substituted by chlorine atoms or $C_1$–$C_9$-alkyl groups, examples being 4-chlorophenol, 2-methylphenol, or 4-tert-butylphenol, or by condensation with bisphenols, those of the type specified above.

III) Poly(N-glycidyl) compounds, obtainable by dehydrochlorination of the reaction products of epichlorohydrin with amines containing at least two active hydrogen bound to amino nitrogen atoms. These amines are, for example, aniline, n-butylamine, bis(4-aminophenyl)-methane, m-xylylenediamine or bis(4-methylaminophenyl)methane.

The poly(N-glycidyl) compounds also include triglycidyl isocyanurate, N,N'-diglycidyl derivatives of cycloalkylene ureas, such as ethylene urea or 1,3-propylene urea, and diglycidyl derivatives of hydantoins, such as of 5,5-dimethylhydantoin.

IV) Poly(S-glycidyl) compounds, for example di-S-glycidyl derivatives derived from dithiols such as ethane-1,2-dithiol or bis(4-mercaptomethylphenyl) ether.

V) Cycloaliphatic epoxy resins, for example bis(2,3-epoxycyclopentyl)ether, 2,3-epoxycyclopentyl glycidyl ether, 1,2-bis(2,3-epoxycyclopentyloxy)ethane or 3,4-epoxycyclohexylmethyl 3',4'-epoxycyclohexanecarboxylate.

However, it is also possible to use epoxy resins in which the 1,2-epoxide groups are attached to different heteroatoms and/or functional groups; these compounds include, for example, the N,N,O-triglycidyl derivative of 4-aminophenol, the glycidyl ether glycidyl ester of salicylic acid, N-glycidyl-N'-(2-glycidyloxypropyl)-5,5-dimethylhydantoin or 2-glycidyloxy-1,3-bis(5,5-dimethyl-1-glycidylhydantoin-3-yl)propane.

Mixtures of epoxy resins can also be used as component B).

A composition wherein component B) is a epoxy resin or a mixture of different epoxy resins therefore also conforms to this invention.

The compositions comprise the photoinitiator, component A), preferably in an amount of from 0.01 to 10% by weight, based on the component B).

In addition to the photoinitiator, component A), the photopolymerisable mixtures may include different additives. Examples of these are thermal inhibitors which are intended to prevent premature polymerisation, such as hydroquinone, hydroquinone derivatives, p-methoxyphenol, β-naphthol or sterically hindered phenols such as 2,6-di(tert-butyl)-p-cresol, for example. To increase the dark storage stability it is possible, for example, to use copper compounds, such as copper naphthenate, stearate or octoate, phosphorus compounds, such as triphenylphosphine, tributylphosphine, triethyl phosphite, triphenyl phosphite or tribenzyl phosphite, quarternary ammonium compounds, such as tetramethylammonium chloride or trimethylbenzylammonium chloride, or hydroxylamine derivatives, such as N-diethylhydroxylamine. To exclude atmospheric oxygen during polymerisation it is possible to add paraffin or similar waxlike substances which, owing to their lack of solubility in the polymer, migrate to the surface at the beginning of polymerisation where they form a transparent surface layer which prevents the ingress of air. It is likewise possible to apply an oxygen-impermeable layer. Light stabilisers, which can be added in a small amount, are UV absorbers such as those, for example, of the hydroxyphenylbenzotriazole, hydroxyphenylbenzophenone, oxalamide or hydroxyphenyl-s-triazine type. Individual compounds or mixtures of these compounds can be used, with or without the use of sterically hindered amines (HALS).

Illustrative examples of such UV absorbers and light stabilisers are the following:

1. 2-(2'-Hydroxyphenyl)benzotriazoles, for example 2-(2'-hydroxy-5'-methylphenyl)-1,2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotrazole, 2-(3',5'-bis-($\alpha,\alpha$-dimethylbenzyl)-2'-hydroxyphenyl)benzotriazole, a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethyhexyloxy)carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$]$_2$— where R=3'-tert-butyl-4'-hydroxy-5'-2H-benzotriazol-2-ylphenyl.

2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxy-cinnamate, butyl $\alpha$-cyano-$\beta$-methyl-p-methoxy-cinnamate, methyl $\alpha$-carbomethoxy-p-methoxycinnamate and N-($\beta$-carbomethoxy-$\beta$-cyanovinyl)-2-methylindoline.

5. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tertoctylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione.

6. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanlide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

7. 2-(2-Hydroxyphenyl)-1.3.5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl)-4,4'-biphenylene diphosphonite, 6-isooctyloxy-2,4,8,10-tetra-tert-butyl-12H-dibenz-[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite.

Illustrative Examples of Further Additives are:

Fillers and reinforcing agents, for example, calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibres.

Other additives, for example, plasticisers, lubricants, emulsifiers, pigments, rheology additives, catalysts, flow-control agents, optical brighteners, flameproofing agents, antistatic agents and blowing agents.

In addition to the additives indicated above it is also possible for additional coinitiators to be present. In general these are dyes which improve the overall quantum yield by means, for example, of energy transfer or electron transfer. Examples of suitable dyes which can be added as coinitiators are triarylmethanes, for example malachite green, indolines, thiazines, for example methylene blue, xanthones, thioxanthones, oxazines, acridines oder phenazines, for example safranine, and rhodamines of formula

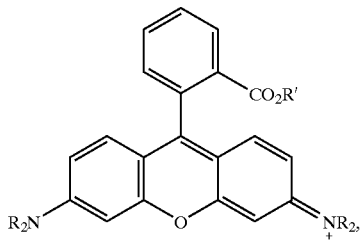

wherein R is alkyl or aryl, and R' is hydrogen, an alkyl or aryl radical, for example Rhodamine B, Rhodamine 6G or Violamine R, and also Sulforhodamine B or Sulforhodamine G.

Preference is given to thioxanthones, oxazine, acridines, phenazines and rhodamines. Also suitable are in this connection combinations of dyes with borates, as described, inter alia, in U.S. Pat. No. 4,772,530, GB 2307474, GB 2307473, GB 2307472 and EP 775706.

In addition to the above-described base-catalysable (curable) binders, component B), the composition may also include other binders as well. It is possible to use, for example, further olefinically unsaturated compounds. The unsaturated compounds may include one or more olefinic double bonds. They may be of low molecular mass (monomeric) or higher molecular mass (oligomeric). Examples of monomers having a double bond are alkyl acrylates or hydroxyalkyl acrylates or alkyl methacrylates or hydroxyalkyl methacrylates, such as methyl, ethyl, butyl, 2-ethylhexyl or 2-hydroxyethyl acrylate, isobornyl acrylate, methyl methacrylate or ethyl methacrylate. Silicone acrylates are also of interest. Further examples are acrylonitrile, acrylamide, methacrylamide, N-substituted (meth) acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers having several double bonds are the diacrylates of ethylene glycol, propylene glycol, neopentyl glycol, hexamethylene glycol or bisphenol A, 4,4'-bis(2-acryloyoxyethoxy)diphenylpropane, trimethylolpropane triacrylate, pentaerythritol triacrylate or pentaerythritol tetraacrylate, vinyl acrylate, divinyl benzene, divinyl succinate, diallyl phthalate, triallyl phosphate, triallyl isocyanurate or tris(2-acryloylethyl)isocyanurate.

Examples of polyunsaturated compounds of high molecular mass (oligomers) are acrylated epoxy resins, acrylated polyesters or polyesters containing vinyl ether groups or epoxy groups, polyurethanes and polyethers. Further examples of unsaturated oligomers are unsaturated polyester resins which are mostly prepared from maleic acid, phthalic acid and one or more diols and have molecular weights of about 500 to 3000. In addition it is also possible to employ vinyl ether monomers and oligomers, and also maleate-terminated oligomers with polyester, polyurethane, polyether, polyvinyl ether and epoxy main chains. In particular, combinations of vinyl ether-carrying oligomers and polymers as are described in WO 90/01512 are very suitable. Also suitable are copolymers of vinyl ether and maleic acid-functionalised monomers. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, such as unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and mixtures of one or more such polymers.

If, in addition, use is made of such radically curable monomers, oligomerstpolymers then it is judicious to add a further photoinitiator which dissociates into radicals. Such photoinitiators are known and are produced industrially. Examples are benzophenone, benzophenone derivatives, acetophenone, acetophenone derivatives, for example α-hydroxycycloalkyl phenyl ketones, dialkoxyacetophenones, α-hydroxy- or α-aminoacetophenones, 4-aroyl-1,3-dioxolanes, benzoin alkym ethers and benzil ketals, monoacyl phosphine oxides, bisacylphosphine oxides, ferrocenium compounds or titanocenes.

Examples are specified in EP-A-284 561. Polymer systems of this kind, in which curing/crosslinking takes place by different mechanisms, are also referred to as hybrid systems.

It is also possible to add non-reactive binders to the novel compositions, which is particularly judicious if the photopolymerisable compounds are liquid or viscous substances. The amount of the non-reactive binder can be, for example, 5–95%, preferably 10–90% and, in particular, 40–90% by weight, based on the overall solids content. The choice of non-reactive binder is made in accordance with the field of use and with the properties required for this use, such as the possibility for development in aqueous and organic solvent systems, adhesion to substrates, and sensitivity to oxygen.

Examples of suitable binders are polymers having a molecular weight of around 5000–2,000,000, preferably 10,000–1,000,000. Examples are: homo- and copolymeric acrylates and methacrylates, for example copolymers of methyl methacrylate/ethyl acrylate/methacrylic acid, poly (alkyl methacrylates), poly(alkyl acrylates); cellulose esters and ethers, such as cellulose acetate, cellulose acetate butyrate, methylcellulose, ethylcellulose; polyvinylbutyral, polyvinylformal, cyclised rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylenevinyl acetate), polymers such as polycaprolactam and poly(hexamethylene adipamide) and polyesters such as poly(ethylene glycol terephtalate) and poly(hexamethylene glycol succinate).

The invention additionally provides a method of carrying out base-catalysed reactions which comprises exposing a novel composition as described above to light having a wavelength of 200 nm to 650 nm.

In some cases it may be advantageous to carry out heating during or after exposure to light.

In this way it is possible in many cases to accelerate the crosslinking reaction.

The sensitivity of the novel compositions to light generally extends from about 200 nm through the UV region and into the infrared region (about 20,000 nm, in particular 1200 nm) and therefore spans a very broad range. Suitable radiation comprises, for example, sunlight or light from artificial light sources. Therefore, a large number of very different types of light source can be used. Both point sources and flat radiators (lamp carpets) are suitable. Examples are carbon arc lamps, xenon arc lamps, medium-pressure, high-pressure and low-pressure mercury lamps, doped if desired with metal halides (metal halogen lamps), microwave-excited metal vapour lamps, excimer lamps, superactinic fluorescent tubes, fluorescent lamps, incandescent argon lamps, electronic flashlights, photographic flood. lamps, electron beams and X-rays, produced by means of synchrotrons or laser plasma. The distance between the lamp and the substrate according to the invention which is to be exposed can vary depending on the application and on the type and/or power of the lamp, for example between 2 cm and 150 cm. Also especially suitable are laser light sources, for example excimer lasers. Lasers in the visible region or in the IR region can also be employed. Very advantageous here is the high sensitivity of the novel materials and the possibility of adapting a dye as coinitiator to the laser line. By this method it is possible to produce printed circuits in the electronics industry, lithographic offset printing plates or relief printing plates, and also photographic image recording materials.

The novel compositions can be employed for various purposes, for example as printing inks, as clearcoats, as white paints, for example for wood or metal, as coating materials, inter alia for paper, wood, metal or plastic, as powder coatings, as daylight-curable coatings for marking buildings and roads, for photographic reproduction processes, for holographic recording materials, for image recording processes or for the production of printing plates which can be developed using organic solvents or aqueous-alkaline media, for the production of masks for screen printing, as dental filling materials, as adhesives, including pressure-sensitive adhesives, as laminating resins, as etch resists or permanent resists and as solder masks for electronic circuits, for the production of three-dimensional articles by mass curing (UV curing in transparent moulds) or by the stereolithography process, as is described, for example, in U.S. Pat. No. 4,575,330, for the preparation of composite materials (for example styrenic polyesters, which may contain glass fibres and/or other fibres and other assistants) and other thick-layer compositions, for the coating or encapsulation of electronic components, or as coatings for optical fibres.

In paint systems, it is common to use mixtures of a prepolymer with polyunsaturated monomers which also contain a monounsaturated monomer. The prepolymer here is primarily responsible for the properties of the coating film, and varying it allows the skilled worker to influence the properties of the cured film. The polyunsaturated monomer functions as a crosslinker, which renders the coating film insoluble. The monounsaturated monomer functions as a reactive diluent, by means of which the viscosity is reduced without the need to use a solvent.

Unsaturated polyester resins are mostly used in two-component systems in conjunction with a monounsaturated monomer, preferably styrene. For photoresists, specific one-component systems are frequently employed, for example polymaleinimides, polychalcones or polyimides, as described in DE-A-2 308 830.

The novel photocurable compositions are suitable, for example, as coating materials for substrates of all kinds, examples being wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$, on which it is the intention to apply a protective coating or, by imagewise exposure, an image.

The substrates can be coated by applying a liquid composition, a solution or suspension to the substrate. The choice of solvent and the concentration depend predominantly on the type of composition and the coating process. The solvent should be inert: in other words, it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

Using known coating processes, the solution is applied uniformly to a substrate, for example by spin coating, dip coating, knife coating, curtain coating, brushing, spraying, especially by electrostatic spraying and reverse roll coating, and by electrophoretic deposition. It is also possible to apply the photosensitive layer to a temporary, flexible support and then to coat the final substrate, for example a copper-clad circuit board, by means of layer transfer via lamination.

The amount applied (layer thickness) and the nature of the substrate (layer support) are functions of the desired field of application. The range of layer thicknesses generally comprises values from about 0.1 $\mu$m to more than 100 $\mu$m.

The novel radiation-sensitive compositions can also be subjected to imagewise exposure. In this case they are used as negative resists. They are suitable for electronics (galvanoresists, etch resists and solder resists), for the production of printing plates, such as offset printing plates, flexographic and relief printing plates or screen printing plates, for the production of marking stamps, and can be used for moulded article etching or as micro resists in the production of integrated circuits. There is a correspondingly wide range of variation in the possible layer supports and in the processing conditions of the coated substrates.

The term "imagewise" exposure relates both to exposure through a photomask containing a predetermined pattern, for example a slide, exposure by a laser beam which is moved under computer control, for example, over the surface of the coated substrate and so generates an image, and irradiation with computer-controlled electron beams.

Following the imagewise exposure of the material and prior to developing, it may be advantageous to carry out a brief thermal treatment, in which only the exposed parts are thermally cured. The temperatures employed are generally 50–150° C. and preferably 80–130° C.; the duration of the thermal treatment is generally between 0.25 and 10 minutes.

A further field of use for photocuring is that of metal coating, for example the surface-coating of metal panels and tubes, cans or bottle tops, and photocuring on polymer coatings, for example of floor or wall coverings based on PVC.

Examples of the photocuring of paper coatings are the colourless varnishing of labels, record sleeves or book covers.

This invention also relates to the use of a compound of formula I

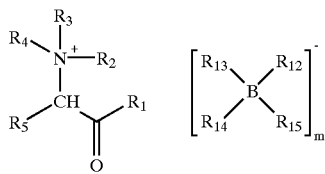

as photoinitiator for photochemically induced base-catalysed addition reactions or substitution reactions, in particular for curing moulded articles made from composite compositions, wherein $R_1$, $R_2$, $R_3$, $R_4$, $R_5$, $R_{12}$, $R_{13}$, $R_{14}$, $R_{15}$ and m have the meanings and preferred meanings stated above.

Another subject of this invention is the above-mentioned use for the preparation of coatings, moulded articles or photostructured layers.

The composite usually consists of a self-supporting matrix material, for example a glass fibre fabric, or also e.g. vegetable fibres [cf K.-P. Mieck, T. Reussmann in Kunststoffe 85 (1995), 366–370], which is impregnated with the photocuring formulation. Moulded articles made from composites produced with the novel compounds attain a high level of mechanical stability and resistance. The novel compounds can also be used as photocuring agents in moulding, impregnating and coating compositions, such as are described in EP-A-7086. Such compositions are, for example, gel coat resins, which are subject to stringent requirements regarding their curing activity and yellowing resistance, and fibre-reinforced moulded articles, such as light-diffusing panels which are planar or which have lengthwise or crosswise corrugation.

Examples and preferences of base-catalysed addition reactions or substitution reactions are stated above.

In another of its aspects, this invention relates to a coated substrate which has been coated on at least one surface with a composition as described above, and to a process for the photographic production of relief images, in which a coated substrate is subjected to imagewise exposure and then the unexposed areas are removed with a solvent. Of particular interest in this context is the above-mentioned exposure by means of a laser beam.

This invention also relates to the use of the novel compounds for the preparation of coatings, moulding compositions or photostructured layers.

In another of its aspects, this invention relates to polymerised or crosslinked novel compositions.

The following Examples illustrate the invention in more detail. As in the remainder of the description and in the claims, parts and percentages are by weight unless stated otherwise. If alkyl or alkoxy radicals having more than three carbon atoms are indicated without reference to their isomeric form, then the respective n-isomers are meant.

The following abbreviations are used in the Examples:
"Ph" for phenyl, "Me" for methyl, "Et" for ethyl, "Hex" for hexyl, "Ar" for aryl, "DMSO" for dimethylsulfoxide, "U.V." for ultraviolet spectra, "I.R." for infrared spectra, "$^1$H NMR" for hydrogen nuclear magnetic resonance spectra (indication of the shift values in "$^{13}$C NMR" for carbon nuclear magnetic resonance spectra (indication of the shift values in ppm)

EXAMPLES A

Preparation of the Bromides and Iodides

General Procedure

One equivalent of nitrogenous base is stirred into diethyl ether at room temperature. One equivalent of a solution of the corresponding α-bromoketone in toluene is added and the reaction mixture is stirred for one hour. The precipitated bromide is filtered, washed with diethyl ether and the solvent is removed under vacuum, giving the product in 80 to 90% yields.

In the Examples, the extinction coefficients e denotes the molar extinction coefficients in the unit I/mol cm.

EXAMPLE A1

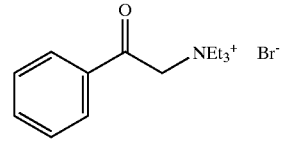

Analysis for $C_{14}H_{22}NOBr$: calculated: C 56.01; H 7.39; N 4.67; Br 26.61. found: C 56.02; H 7.34; N 4.45; Br 26.82.

U.V. (CHCl$_3$) max. at 255 nm ($\epsilon$13300).

$^1$H NMR (CDCl$_3$): 8.03 (2H, d, ArH), 7.38 (1H, t, ArH), 7.23 (2H, m, ArH), 5.20 (2H, s, CH$_2$), 3.69 (6H, q, CH$_2$CH$_3$) and 1.16 (9H, t, CH$_2$CH$_3$).

EXAMPLE A2

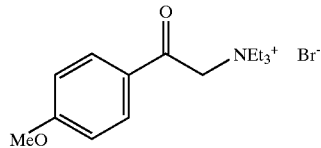

U.V. (CHCl$_3$) max. at 294 nm ($\epsilon$16800).

$^1$H NMR (CDCl$_3$): 8.37 (2H, d, ArH), 7.00 (2H, d, ArH), 5.44 (2H, s, CH$_2$), 3.88 (9H, q, and s, CH$_2$CH$_3$ and OCH$_3$) and 1.41 (9H, t, CH$_2$CH$_3$).

EXAMPLE A3

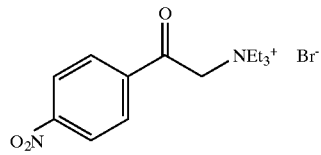

U.V. (MeOH) max. at 261 nm ($\epsilon$12800).

$^1$H NMR (CDCl$_3$): 8.63 (2H, d, ArH), 8.30 (2H, d, ArH), 5.84 (2H, s, CH$_2$), 3.86 (6H, q, CH$_2$CH$_3$) and 1.41 (9H, t, CH$_2$CH$_3$).

EXAMPLE A4

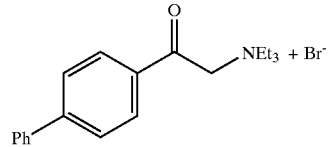

U.V. (CHCl$_3$) max. at 243 nm ($\epsilon$3000) and 305 nm ($\epsilon$24000).

$^1$H NMR (CDCl$_3$): 8.41 (2H, d, ArH), 7.74 (2H, d, ArH), 7.58 (2H, d, ArH), 7.44 (3H, m, ArH), 5.57 (2H, s, CH$_2$), 3.87 (6H, q, CH$_2$CH$_3$) and 1.42 (9H, t, CH$_2$CH$_3$).

EXAMPLE A5

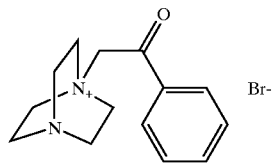

U.V. (H₂O) max. at 252 nm (ε14100).

¹H NMR (D₂O): 8.01 (2H, d, ArH), 7.79 (1H, t, ArH), 7.66 (2H, t, ArH), 3.81 (6H, t, NCH₂) and 3.31 (6H, t, NCH₂).

EXAMPLE A6

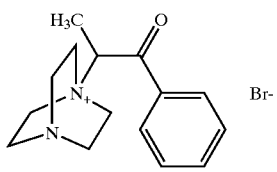

Analysis for $C_{15}H_{21}N_2OBr$: calculated C 55.39; H 6.51; N 8.61; Br 24.57; found: C 55.11; H 6.59; N 8.70; Br 24.65.

U.V. (CHCl₃) max. at 259 nm (ε14000).

¹H NMR (CDCl₃): 8.15 (2H, d, ArH), 7.50 (1H, t, ArH), 7.37 (2H, t, ArH), 6.03 (1H, q, CH), 3.99 (3H, t, NCH₂), 3.85 (3H, t, NCH₂), 3.14 (6H, m, NCH₂) and 1.59 (3H, d, CH₃).

EXAMPLE A7

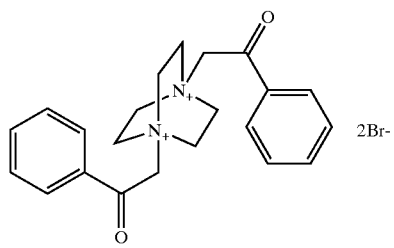

U.V. (H₂O) max. at 254 nm (ε28200).

¹H NMR (D₂O): 8.01 (4H, d, ArH), 7.80 (2H, t, ArH), 7.62 (4H, t, ArH) and 4.50 (12H, s, NCH₂).

EXAMPLE A8

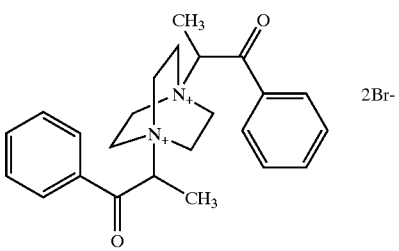

U.V. (MeOH) max. at 256 nm (ε23500).

¹H NMR (D₂O): 8.07 (4H, d, ArH), 7.82 (2H, t, ArH), 7.66 (4H, t, ArH), 5.74 (2H, q, CH), 4.53 (6H, m, NCH₂), 4.30 (6H, m, NCH₂) and 1.85 (6H, d, CH₃).

EXAMPLE A9

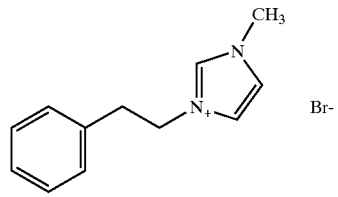

U.V. (CD₃CN) max. at 245 (ε14600) and 281 (ε1500).

¹H NMR (DMSO): 9.06 (1H, s, ArH), 8.05 (2H, d, ArH), 7.80–7.60 (5H, m, ArH), 6.06 (2H, s, CH₂) and 3.95 (3H, s, NCH₃).

EXAMPLE A10

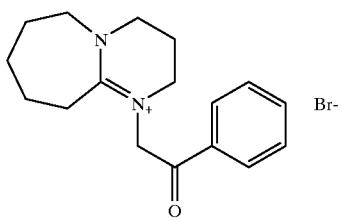

¹H NMR (CDCl₃): 8.07 (2H, d, ArH), 7.63 (1H, t, ArH), 7.50 (2H, t, ArH), 5.57 (2H, s, CH₂), 3.67 (4H, m, NCH₂) and 3.5–1.3 (12H, m, CH₂).

EXAMPLE A11

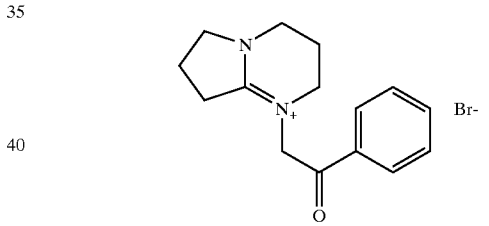

¹H NMR (CDCl₃): 8.02 (2H, d, ArH), 7.61 (1H, t, ArH), 7.48 (2H, t, ArH), 5.33 (2H, s, CH₂), 3.84 (2H, t, NCH₂), 3.67 (4H, m, NCH₂), 3.14 (2H, m, CH₂) and 2.3–2.1 (4H, m, CH₂).

EXAMPLE A12

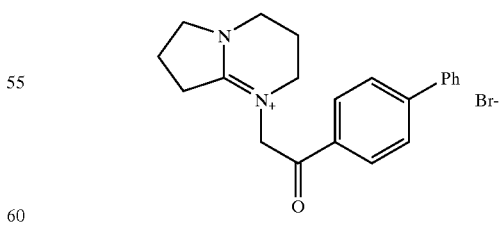

U.V. (CHCl₃) max. at 297 nm (ε22000).

¹H NMR (CDC₁₃): 8.08 (2H, d, ArH), 7.67 (2H, d, ArH), 7.54 (2H, d, ArH), 7.37 (3H, m, ArH), 5.37 (2H, s, CH₂), 3.84 (2H, t, NCH₂), 3.54 (4H, m, NCH₂), 3.11 (2H, m, CH₂) and 2.3–2.1 (4H, m, CH₂).

EXAMPLE A13

¹H NMR (CDCl₃): 8.57 (1 H, s, ArH), 8.07 (2H, d, ArH), 7.64–7.50 (6H, m, ArH), 4.96 (2H, s, CH₂), 3.94 (2H, t, NCH₂), 3.82 (2H, t, NCH₂), 3.65 (4H, t, CH₂), 3.45–3.30 (6H, m, CH₂) and 2.4–2.1 (6H, m, CH₂).

EXAMPLE A14

U.V. (CHCl₃) max. at 245 nm (ε30500), 291 nm (ε22300), 371 nm (ε17500) and 403 nm (ε14900).

¹H NMR (CDCl₃): 9.10 (1H, d, ArH), 8.66 (1H, d, ArH), 8.3–7.8 (7H, m, ArH), 5.56 (2H, s, CH₂), 3.85 (2H, t, NCH₂), 3.57 (2H, t, NCH₂), 3.23 (2H, t, CH₂) and 2.4–2.1 (6H, m, CH₂).

The α-iodoketones are prepared from commercially available α-bromoketones via a Finkelstein reaction. The iodides are the prepared in analogy to the bromides described above.

EXAMPLE A15

Analysis for C₁₁H₁₆NOI: calculated C 43.30; H 5.29; N 4.59; I 41.59. found: C 43.32; H 5.22; N 4.59; I 41.82.

U.V. (CHCl₃) max. at 246 nm (ε25800).

¹H NMR (CD₃CN): 8.00 (2H, d, ArH), 7.70 (1H, t, ArH), 7.57 (2H, t, ArH), 5.18 (2H, s, CH₂) and 3.37 (9H, s, CH₃).

EXAMPLE A16

U.V. (CHCl₃) max. at 249 nm (ε18900).

¹H NMR (CDCl₃): 8.19 (2H, d, ArH), 7.58 (1H, t, ArH), 7.43 (2H, t, ArH), 5.25 (2H, s, CH₂), 3.82 (6H, q, CH₂CH₃) and 1.34 (9H, t, CH₂CH₃).

EXAMPLE A17

U.V. (CHCl3) max. at 245 nm (ε10300) and 295 nm (ε18100).

¹H NMR (CDC₁₃): 8.25 (2H, d, ArH), 6.93 (2H, d, ArH), 5.20 (2H, s, CH₂), 3.82 (9H, q and s, CH₂CH₃ and OCH₃) and 1.37 (9H, t, CH₂CH₃).

EXAMPLE A18

¹H NMR (CDCl₃): 8.59 (2H, d, ArH), 8.32 (2H, d, ArH), 5.68 (2H, s, CH₂), 3.86 (6H, q, CH₂CH₃) and 1.44 (9H, t, CH₂CH₃).

EXAMPLE A19

U.V. (CHCl₃) max. at 244 nm (ε11100) and 305 nm (ε23400).

¹H NMR (CDCl₃): 8.38 (2H, d, ArH), 7.72 (2H, d, ArH), 7.57 (2H, d, ArH), 7.42 (3H, m, ArH), 5.40 (2H, s, CH₂), 3.88 (6H, q, CH₂CH₃) and 1.42 (9H, t, CH₂CH₃).

EXAMPLE A20

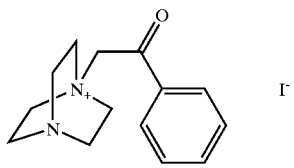

U.V. (MeOH) max. at 249 nm (ε14900).

$^1$H NMR (D$_2$O): 8.00 (2H, d, ArH), 7.78 (1H, t, ArH), 7.64 (2H, t, ArH), 3.81 (6H, t, NCH$_2$) and 3.31 (6H, t, NCH$_2$).

EXAMPLE A21

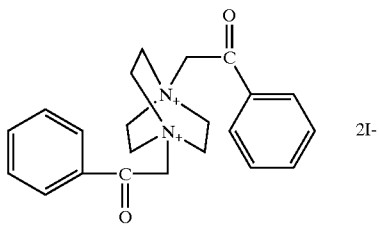

Analysis for C$_{22}$H$_{26}$N$_2$O$_2$I$_2$: calculated C 43.73; H 4.34; N 4.64; I 42.00. found: C 43.29; H 4.24; N 4.29; I 41.82.

U.V. (MeOH) max. at 252 nm (ε28400).

$^1$H NMR (DMSO): 8.04 (4H, d, ArH), 7.79 (2H, t, ArH), 7.64 (4H, t, ArH), 5.55 (4H, s, CH$_2$) and 4.31 (12H, s, NCH$_2$).

EXAMPLE A22

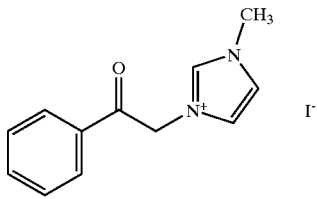

U.V. (CH$_3$CN) max. at 246 (ε27400).

$^1$H NMR (DMSO): 9.03 (1H, s, ArH), 8.05 (2H, d, ArH), 7.80–7.60 (5H, m, ArH), 6.04 (2H, s, CH$_2$) and 3.95 (3H, s, NCH$_3$).

EXAMPLE A23

Analysis for C$_{15}$H$_{17}$N$_2$OI: calculated C 48.93; H 4.65; N 7.61; I 34.46. found: C 48.89; H 4.60; N 7.34; I 34.48.

U.V. (CH$_3$CN) max. at 257 (ε20500), 289 nm (ε26200) and 364 (ε7000).

$^1$H NMR (DMSO): 8.18 (2H, d, ArH), 8.03 (2H, d, ArH), 7.76 (1H, t, ArH), 7.64 (2H, d, ArH), 7.12 (2H, d, ArH), 5.96 (2H, s, CH$_2$) and 3.23 (6H, s, NCH$_3$).

EXAMPLE A24

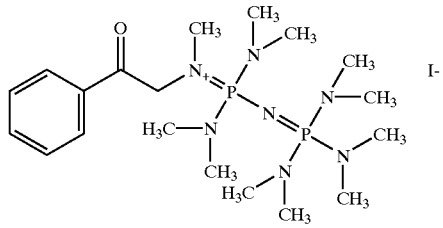

Analysis for C$_{20}$H$_{42}$N$_7$OP$_2$I: calculated C 41.03; H 7.23; N 16.75; I 21.68. found: C 40.62; H 7.49; N 17.10; I 21.56.

EXAMPLE A25

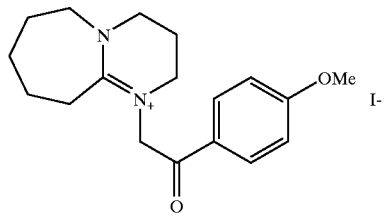

U.V. (CHCl$_3$) max. at 245 nm (ε9500), 288 nm (ε23500) and 366 nm (ε4100).

$^1$H NMR (CDCl$_3$): 7.98 (2H, d, ArH), 6.92 (2H, d, ArH), 5.35 (2H, s, CH$_2$), 3.81 (3H, s, OCH$_3$), 3.65 (4H, m, NCH$_2$) and 3.5–1.3 (12H, m, CH$_2$).

EXAMPLE A26

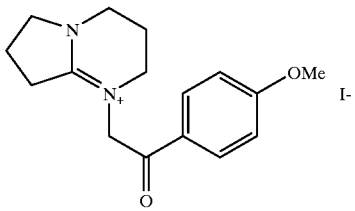

U.V. (CHCl$_3$) max. at 247 nm (ε9800) and 287 nm (ε19500).

$^1$H NMR (CDCl$_3$): 7.97 (2H, d, ArH), 6.95 (2H, d, ArH), 5.14 (2H, s, CH$_2$), 3.85 (5H, m, NCH$_2$ and OCH$_3$), 3.55 (4H, m, NCH$_2$), 3.10 (2H, m, NCH$_2$) and 2.4–2.2 (4H, m, CH$_2$).

EXAMPLE A27

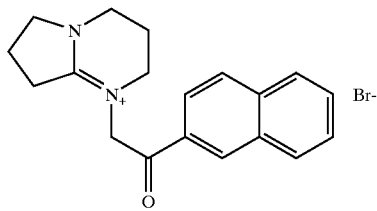

I.R. (KBr): 1690 cm$^{-1}$, 1665 cm$^{-1}$ (C=O).

$^1$H NMR (CDCl$_3$): 8.72 (1H, s, ArH), 8.02 (2H, m, ArH), 7.85(2H, m, ArH), 7.56 (2H, m, ArH), 5.45 (2H, s, CH$_2$), 3.84 (2H, t, NCH$_2$), 3.58 (4H, m, NCH$_2$), 3.17 (2H, m, CH$_2$) and 2.3–2.1 (4H, m, CH$_2$).

EXAMPLE A28

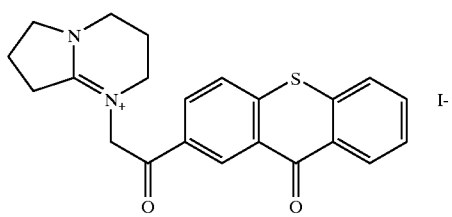

I.R. (KBr): 1695 cm$^{-1}$, 1665 cm$^{-1}$, (C=O), 1640 cm$^{-1}$.

$^1$H NMR (CDCl$_3$): 8.95 (1H, d, ArH), 8.43 (1H, d, ArH), 8.14 (1H, dd, ArH), 7.54 (4H, m, ArH), 5.42 (2H, s, CH$_2$), 3.91 (2H, t, NCH$_2$), 3.71 (2H, t, NCH$_2$), 3.62 (2H, t, NCH$_2$), 3.25 (2H, t, NCH$_2$) and 2.4–2.2 (4H, m, CH$_2$).

Examples B

Preparation of the Borate Salts

General Procedure for the Preparation of the Tetraphenylborates

One equivalent of the bromides is stirred into water at room temperature and one equivalent of an aqueous solution of sodium tetraphenylborate is added. The precipitated tetraphenylborate salt is isolated by filtration, washed with water and dried under vacuum, giving the product in a 95% yield.

EXAMPLE B1

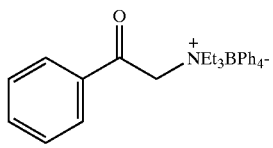

Analysis for C$_{38}$H$_{42}$NOB: calculated: C 84.59; H 7.85; N 2.60; found: C 84.31; H 8.18; N 2.16.

U.V. (CHCl$_3$) max. at 251 nm (ε18900).

$^1$H NMR (CDCl$_3$): 7.63 (3H, m, ArH), 7.28 (10H, m, ArH), 6.94 (8H, t, ArH), 6.80 (4H, t, ArH), 3.78 (2H, s, CH$_2$), 2.81 (6H, q, CH$_2$CH$_3$) and 0.75 (9H, t, CH$_2$CH$_3$). $^{13}$C NMR (CDCl$_3$): 189.93, 165.96, 165.17, 164.39, 163.61, 136.72, 135.49, 133.99, 129.44, 128.43, 128.37, 128.24, 128.04, 127.87, 127.81, 127.66, 127.48, 127.40, 127.37, 126.24, 126.20, 126.16, 126.12, 122.27, 116.68, 58.60, 54.50 and 7.41.

EXAMPLE B2

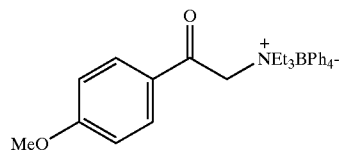

Analysis for C$_{39}$H$_{44}$NO$_2$B: calculated: C 82.24; H 7.79; N 2.46; found: C 82.05; H 8.21; N 2.24.

$^1$H NMR (DMSO): 8.04 (2H, d, ArH), 7.16 (10H, m, ArH), 6.93 (8H, t, ArH), 6.80 (4H, t, ArH), 5.09 (2H, s, CH$_2$), 3.89 (3H, s, OCH$_3$), 3.59 (6H, q, CH$_2$CH$_3$) and 1.20 (9H, t, CH$_2$CH$_3$).

EXAMPLE B3

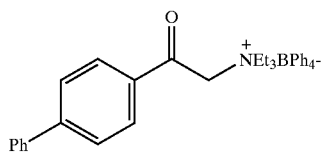

Analysis for C$_{44}$H$_{46}$NOB: calculated: C 85.84; H 7.53; N 2.28; found: C 85.86; H 7.55; N 2.04.

$^1$H NMR (DMSO): 8.15 (2H, d, ArH), 7.95 (2H, d, ArH), 7.81 (2H, d, ArH), 7.50 (3H, m, ArH), 7.17 (8H, m, ArH), 6.93 (8H, t, ArH), 6.80 (4H, t, ArH), 5.21 (2H, s, CH$_2$), 3.62 (6H, q, CH$_2$CH$_3$) and 1.25 (9H, t, CH$_2$CH$_3$).

EXAMPLE B4

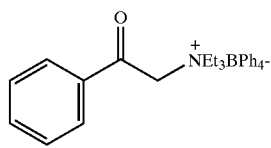

Analysis for C$_{35}$H$_{36}$NOB: calculated: C 84.50; H 7.29; N 2.82; found: C 84.52; H 7.29; N 2.64.

$^1$H NMR (DMSO): 7.99 (2H, d, ArH), 7.77 (1H, t, ArH), 7.63 (2H, t, ArH), 7.18 (8H, m, ArH), 6.93 (8H, t, ArH), 6.79 (4H, t, ArH), 5.27 (2H, s, CH$_2$) and 3.31 (9H, s, CH$_3$).

EXAMPLE B5

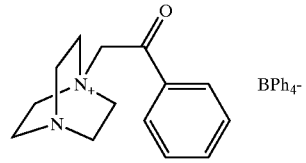

Analysis for C$_{38}$H$_{39}$N$_2$OB: calculated: C 82.90; H 7.14; N 5.09; found: C 82.78; H 7.12; N 4.79.

$^1$H NMR (CD$_3$COCD$_3$): 8.02 (2H, d, ArH), 7.71 (1 H, t, ArH), 7.58 (2H, t, ArH), 7.35 (8H, m, ArH), 6.92 (8H, m, ArH), 6.77 (4H, m, ArH), 3.87 (6H, m, NCH$_2$) and 3.33 (6H, m, NCH$_2$).

EXAMPLE B6

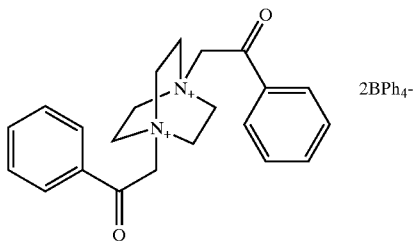

Analysis for $C_{70}H_{66}N_2O_2B_2$: calculated: C 85.02; H 6.73; N 2.83; found: C 84.97; H 6.60; N 2.87.

$^1$H NMR (CD$_3$COCD$_3$): 8.00 (4H, d, ArH), 7.77 (2H, t, ArH), 7.60 (4H, t, ArH), 7.34 (16H, m, ArH), 6.93 (16H, m, ArH), 6.78 (8H, m, ArH), 5.63 (2H, s, CH$_2$) and 4.69 (12H, m, NCH$_2$).

EXAMPLE B7

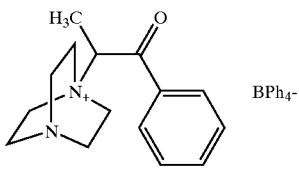

Analysis for $C_{39}H_{41}N_2OB$: calculated: C 82.97; H 7.32; N 4.96; found: C 82.67; H 7.11; N 4.92.

$^1$H NMR (CD$_3$COCD$_3$): 8.00 (2H, d, ArH), 7.67 (1H, t, ArH), 7.50 (2H, t, ArH), 7.22 (8H, m, ArH), 6.79 (8H, m, ArH), 6.64 (4H, m, ArH), 5.45 (1H, q, CH), 3.83 (3H, m, NCH$_2$), 3.57 (3H, m, NCH$_2$), 3.16 (6H, m, NCH$_2$) and 1.65 (3H, d, CH$_3$).

EXAMPLE B8

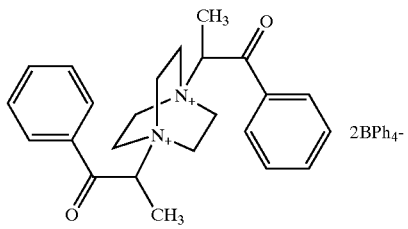

$^1$H NMR (CD$_3$COCD$_3$): 7.97 (4H, d, ArH), 7.66 (2H, t, ArH), 7.51 (4H, t, ArH), 7.22 (16H, m, ArH), 6.79 (16H, m, ArH), 6.65 (8H, m, ArH), 5.88 (2H, m, CH), 4.57 (6H, m, NCH$_2$), 4.35 (6H, m, NCH$_2$) and 1.78 (6H, m, CH$_3$).

EXAMPLE B9

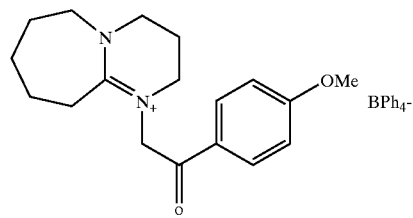

$^1$H NMR (CDCl$_3$): 7.57 (2H, d, ArH), 7.5–6.8 (22H, m, ArH), 3.88 (3H, s, OCH$_3$), 3.85 (2H, s, CH$_2$), 3.23 (2H, m, CH$_2$), 3.06 (3H, m, CH$_2$), 2.87 (1H, m, CH$_2$), 2.53 (2H, t, CH$_2$), 1.87 (2H, m, CH$_2$) and 1.7–1.3 (6H, m, CH$_2$).

EXAMPLE B10

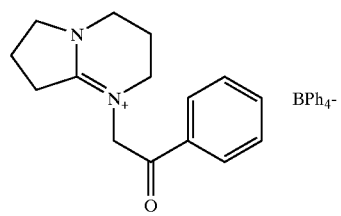

Analysis for $C_{39}H_{39}N_2OB$: calculated: C 83.27; H 6.99; N 4.98; found: C 82.90; H 7.20; N 4.97.

$^1$H NMR (C$_6$D$_6$): 7.78 (3H, m, ArH), 7.61 (5H, m, ArH), 7.15 (14H, m, ArH), 6.77 (3h, m, ArH), 3.35 (2H, s, CH$_2$), 2.22 (2H, q, CH$_2$), 1.8–1.0 (12H, m, CH$_2$) and 0.23 (9H, t, CH$_3$).

EXAMPLE B11

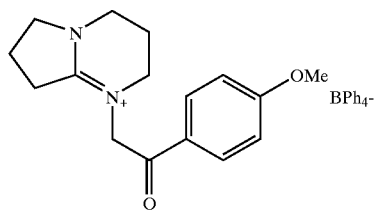

Analysis for $C_{40}H_{43}N_2O_2B$: calculated: C 80.80; H 7.29; N, 4.71; found: C 81.01; H 7.29; N 4.62.

U.V. (CH$_3$CN) max. at 275 nm ($\epsilon$20100).

$^1$H NMR (CDCl$_3$): 7.62 (2H, d, ArH), 7.5–6.8 (22H, m, ArH), 3.90 (3H, s, OCH$_3$), 3.79 (2H, s, CH$_2$), 3.51 (2H, t, CH$_2$), 3.17 (2H, t, CH$_2$), 2.79 (2H, t, CH$_2$), 2.53 (2H, t, CH$_2$) and 1.86 (6H, m, CH$_2$).

EXAMPLE B12

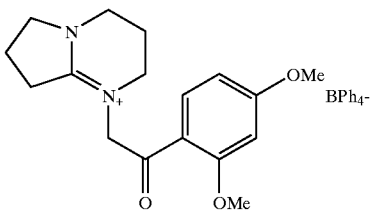

U.V. (CHCl$_3$) max. at 243 nm ($\epsilon$11800), 274 nm ($\epsilon$14900) and 312 nm ($\epsilon$9400).

$^1$H NMR (CDCl$_3$): 7.88 (1H, d, ArH), 7.45 (8H, m, ArH), 6.94 (8H, t, ArH), 6.57 (1H, dd, ArH), 6.41 (1H, d, ArH), 4.07 (2H, s, CH$_2$), 3.86 (3H, s, OCH$_3$), 3.61 (3H, s, OCH$_3$), 3.00 (2H, t, CH$_2$), 2.65 (2H, t, CH$_2$), 2.56 (2H, t, CH$_2$), 1.53 (2H, t, CH$_2$) and 1.30 (6H, m, CH$_2$).

EXAMPLE B13

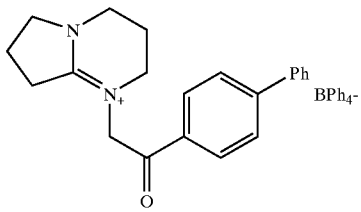

Analysis for C$_{45}$H$_{43}$N$_2$OB: calculated: C 84.63; H 6.79; N 4.39; found: C 84.50; H 6.84; N 4.35.

$^1$H NMR (CDCl$_3$): 7.7–6.7 (29H, m, ArH), 3.71 (2H, s, CH$_2$), 3.08 (2H, t, NCH$_2$), 2.72 (2H, t, NCH$_2$), 2.53 (2H, t, CH$_2$) and 1.7–1.4 (6H, m, CH$_2$).

EXAMPLE B14

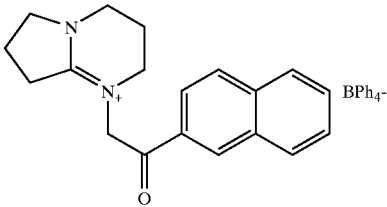

Analysis for C$_{43}$H$_{41}$N$_2$OB: calculated: C 84.31; H 6.75; N 4.57; found: C 84.20; H 6.82; N 4.50.

U.V. (CH$_3$CN) max. at 250 nm ($\epsilon$63000) and 284 nm ($\epsilon$10100).

$^1$H NMR (CD$_3$CN): 8.58 (1H, s, ArH), 8.00 (4H, m, ArH), 7.68 (2H, m, ArH), 7.27 (8H, m, ArH), 6.98 (8H, m, ArH), 6.83 (4H, t, ArH), 5.04 (2H, s, CH$_2$), 3.71 (2H, t, NCH$_2$), 3.40 (4H, m, NCH$_2$), 2.77 (2H, t, CH$_2$) and 2.1–1.8 (6H, m, CH$_2$).

EXAMPLE B15

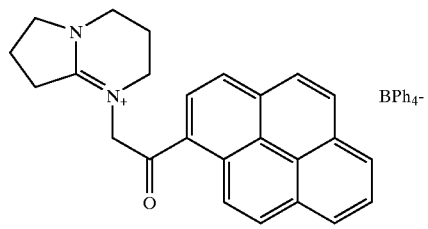

U.V. (CHCl$_3$) max. at 246 nm ($\epsilon$40700), 292 nm ($\epsilon$21100), 374 nm ($\epsilon$16600) and 406 nm ($\epsilon$15600).

EXAMPLE B16

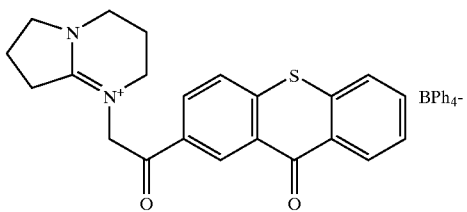

I.R. (KBr): 1695 cm$^{-1}$, 1680 cm$^{-1}$ (C=O), 1665 cm$^{-1}$, 1640 cm$^{-1}$.

$^1$H NMR (CD$_3$COCD$_3$): 9.01 (1H, d, ArH), 8.54 (1H, d, ArH), 8.16 (1H, dd, ArH), 7.86 (1H, d, ArH), 7.78 (2H, dd, ArH), 7.35 (8H, m, ArH), 6.79 (4H, t, ArH), 5.18 (2H, s, CH$_2$), 3.70 (2H, t, NCH$_2$), 3.58 (2H, t, NCH$_2$), 3.40 (2H, dd, NCH$_2$) and 2.7–2.1 (6H, m, CH$_2$).

Preparation of the Tetra(4-Fluorophenyl)borate Salts

One equivalent of the bromides is stirred into water at room temperature and one equivalent of an aqueous solution of sodium tetra(4-fluorophenyl)borate dihydrate is added. The precipitated tetra(4-fluorophenyl)borate salt is isolated by filtration, washed with water and dried under vacuum, giving the product in quantitative yield.

EXAMPLE B17

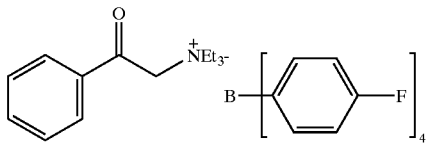

U.V. (CHCl$_3$) max. at 255 nm ($\epsilon$16100).

$^1$H NMR (CDCl$_3$): 7.81 (2H, d, ArH), 7.63 (1H, t, ArH), 7.45 (2H, t, ArH), 7.16 (8H, m, ArH), 6.67 (8H, m, ArH), 4.36 (2H, s, CH$_2$), 3.32 (6H, q, CH$_2$CH$_3$) and 1.08 (9H, t, CH$_2$CH$_3$). $^{13}$C NMR (C$_6$D$_6$): 162.34, 159.20, 137.61, 135.69, 129.57, 128.52, 128.20, 127.88, 116.92, 54.67 and 7.44.

EXAMPLE B18

Analysis for $C_{39}H_{35}N_2OBF_4$: calculated: C 73.82; H 5.56; N 4.41; found: C 73.62; H 5.55; N 4.63.

U.V. $(CHCl_3)$ max. at 246 nm ($\epsilon$20700).

$^1$H NMR $(C_6D_6)$: 7.74 (2H, d, ArH), 7.61 (8H, m, ArH), 7.34–7.15 (3H, m, ArH), 6.91 (8H, m, ArH), 4.09 (2H, s, $CH_2$), 2.22 (2H, q, $CH_2$), 1.8–1.0 (12H, m, $CH_2$) and 0.23 (9H, t, $CH_3$). $^{13}$C NMR $(CDCl_3)$: 197.79, 167.20, 163.43, 141.89, 139.85, 134.37, 133.53, 117.48, 117.43, 117.19, 117.15, 64.01, 59.94, 51.83, 47.73, 35.70, 24.15 and 23.16.

Preparation of Tetra(2,3,4,5,6-Pentafluorolphenyl) borate Salt

One equivalent of the bromides is stirred into water at room temperature and one equivalent of a methanolic/aqueous solution (3/1) of tetraethyl ammonium-tetra(2,3,4,5,6-pentafluoro phenyl)borate is added. The precipitated tetra(2,3,4,5,6-pentafluorophenyl)borate is isolated by filtration, washed with water and dried under vacuum, giving the product in a 75% yield.

EXAMPLE B19

U.V. $(CHCl_3)$ max. at 256 nm ($\epsilon$12800).

$^1$H NMR $(CDCl_3)$: 7.85 (2H, d, ArH), 7.63 (1H, t, ArH), 7.44 (2H, t, ArH), 4.60 (2H, s, $CH_2$), 3.52 (6H, q, $CH_2CH_3$) and 1.17 (9H, t, $CH_2CH_3$).

Preparation of tri(3-Fluorophenyl)hexylborate Salt

One equivalent of the bromides is stirred into water at room temperature and one equivalent of a methanolic solution of tetramethyl ammonium-tri(3-fluorophenyl)hexylborate is added. The precipitated tri(3-fluorophenyl)hexylborate salt is isolated by filtration, washed with water and dried under vacuum, giving the product in a 75% yield.

EXAMPLE B20

U.V. $(CHCl_3)$ max. at 252 nm ($\epsilon$17600).

$^1$H NMR $(CDCl_3)$: 7.68 (3H, m, ArH), 7.49 (2H, t, ArH), 7.22 (3H, d, ArH), 6.99 (6H, m, ArH), 6.53 (3H, m, ArH), 3.78 (2H, s, $CH_2$), 2.99 (6H, q, $CH_2CH_3$) and 1.4–0.7 (22H, m, $CH_2$ and $CH_3$).

EXAMPLE B21

U.V. $(CHCl_3)$ max. Bei 257 nm ($\epsilon$89900), 369 nm ($\epsilon$6300) and 388 nm ($\epsilon$5800).

$^1$H NMR $(CDCl_3)$: 8.62 (1H, s, ArH), 8.11 (2H, m, ArH), 7.62–7.45 (6H, m, ArH), 7.08 (3h, m, ArH), 6.87 (6H, m, ArH), 6.41 (3H, m, ArH), 4.24 (2H, s, $CH_2$), 3.44 (2H, t, $NCH_2$), 3.15 (2H, t, $NCH_2$), 3.04 (2H, t, $NCH_2$), 2.51 (2H, t, $CH_2$), 2.01–1.7 (4H, m, $CH_2$) and 1.3–0.7 (13H, m, $CH_2$ and $CH_3$).

EXAMPLE B22

U.V. $(CHCl_3)$ max. at 256 nm ($\epsilon$55600), 298 nm ($\epsilon$11400) and 346 nm ($\epsilon$2400).

$^1$H NMR $(CDCl_3)$: 8.21 (1H, s, ArH), 8.01 (1H, d, ArH), 7.90 (2H, m, ArH), 7.81 (1 H, d, ArH), 7.64 (2H, m, ArH), 7.21 (3H, m, ArH), 6.94 (6H, m, ArH), 6.49 (3H, m, ArH), 4.16 (2H, s, $CH_2$), 3.44 (2H, t, $NCH_2$), 3.06 (2H, t, $NCH_2$), 2.87 (2H, t, $NCH_2$), 2.14 (2H, t, $CH_2$), 2.0–1.7 (4H, m, $CH_2$) and 1.3–0.7 (13H, m, $CH_2$ and $CH_3$).

EXAMPLE B23

U.V. $(CHCl_3)$ max. at 246 nm ($\epsilon$34800), 292 nm ($\epsilon$24100), 371 nm ($\epsilon$18500) and 404 nm ($\epsilon$15800).

$^1$H NMR $(CDCl_3)$: 9.16 (1H, d, ArH), 8.3–7.9 (8H, m, ArH), 7.3–6.8 (9H, m, ArH), 6.50 (3H, m, ArH), 4.32 (2H, s, $CH_2$), 3.36 (2H, t, $NCH_2$), 3.01 (2H, t, $NCH_2$), 2.91 (2H, t, $NCH_2$), 2.18 (2H, t, $CH_2$), 2.0–1.7 (4H, m, $CH_2$) and 1.3–0.6 (13H, m, $CH_2$ and $CH_3$).

EXAMPLE B24

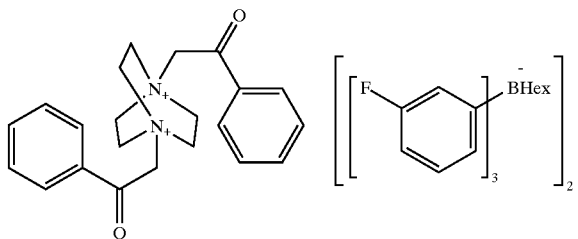

¹H NMR (CD₃COCD₃): 8.00 (4H, d, ArH), 7.77 (2H, t, ArH), 7.60 (4H, t, ArH), 7.34 (16, m, ArH), 6.93 (16H, m, ArH), 6.78 (8H, m, ArH), 5.63 (2H, s, CH₂) and 4.69 (12H, m, NCH₂), 7.22 (3H, d, ArH), 6.99 (6H, m, ArH), 6.53 (3H, m, ArH), 3.78 (2H, s, CH₂), 2.99 (6H, q, CH₂CH₃) and 1.4–0.7 (22H, m, CH₂ and CH₃).

EXAMPLE B25

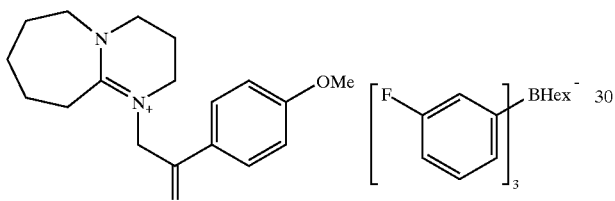

¹H NMR (CDCl₃): 7.47 (2H, d, ArH), 7.0–6.4 (14H, m, ArH), 4.04 (2H, s, CH₂), 3.69 (3H, s, OCH₃), 3.16 (2H, m, CH₂), 3.00 (3H, m, CH₂), 2.85 (1H, m, CH₂), 2.62 (2H, m, CH₂), 1.91 (2H, m, CH₂) and 1.7–0.6 (19H, m, CH₂).

EXAMPLE B26

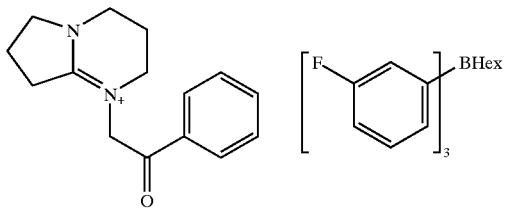

U.V. (CHCl₃) max. at 247 nm (ε24100).

¹H NMR (CDCl₃): 7.62 (3H, m, ArH), 7.44 (2H, m, ArH), 7.05 (3H, m, ArH), 6.86 (6H, m, ArH), 6.42 (3H, m, ArH), 3.97 (2H, s, CH₂), 2.62 (2H, t, NCH₂), 2.50 (2H, t, NCH₂), 2.33 (2H, t, NCH₂), 1.74 (2H, t, CH₂), 1.29 (2H, m, CH₂) and 1.15 (2H, m, CH₂).

EXAMPLE B27

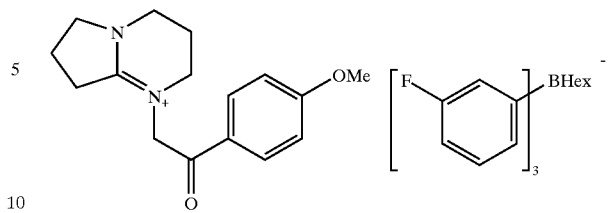

¹H NMR (CDCl₃): 7.62 (2H, d, ArH), 7.08 (3H, m, ArH), 6.86 (8H, m, ArH), 6.42 (3H, m, ArH), 3.96 (2H, s, CH₂), 3.81 (3H, s, OCH₃), 3.30 (2H, t, CH₂), 2.94 (2H, t, CH₂), 2.75 (2H, t, CH₂), 2.03 (2H, t, CH₂), 1.76 (4H, m, CH₂) and 1.3–0.6 (13H, m, CH₂ and CH₃).

Preparation of Tetra(3-Methylphenyl)borate Salt

One equivalent of the bromides is stirred into dimethylformamide at room temperature and one equivalent of a solution of cesium tetrakis(3-methylphenyl)borate in dimethylformamide is added. The precipitated tetrakis(3-methylphenyl)borate salt is isolated by filtration, washed several times with water and dried under vacuum.

EXAMPLE B28

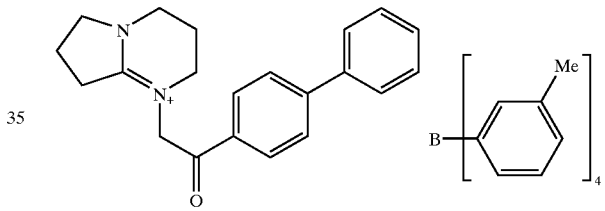

U.V. (CHCl₃) max. at 245 nm (ε17200) and 298 nm (ε23000).

¹H NMR (CDCl₃): 7.57 (5H, m, ArH), 7.43 (4H, m, ArH), 7.31 (4H, m, ArH), 7.21 (4h, m, ArH), 6.77 (4H, t, ArH), 6.57 (4H, d, ArH), 3.51 (2H, s, CH₂), 3.02 (2H, t, CH₂), 2.64 (2H, t, CH₂), 2.49 (2H, t, CH₂), 2.05 (12H, s, CH₃) and 1.7–1.4 (9H, m, CH₃).

EXAMPLE B29

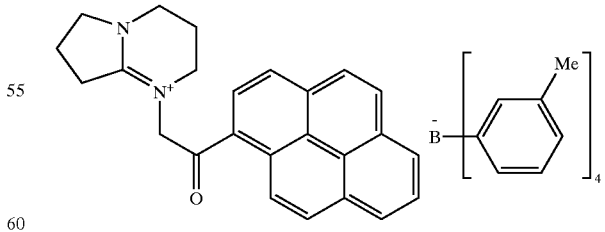

¹H NMR (CDCl₃): 9.16 (1H, d, ArH), 8.38 (1H, d, ArH), 8.28–8.03 (7H, m, ArH), 7.44 (4H, m, ArH), 7.21 (4H, m, ArH), 7.77 (4H, t, ArH), 6.57 (4H, d, ArH), 3.51 (2H, s, CH₂), 3.02 (2H, t, CH₂), 3.64 (2H, t, CH₂), 2.49 (2H, t, CH₂), 2.05 (12H, s, CH₃) and 1.7–1.4 (9H, m, CH₃).

EXAMPLE B30

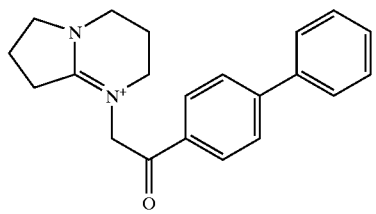 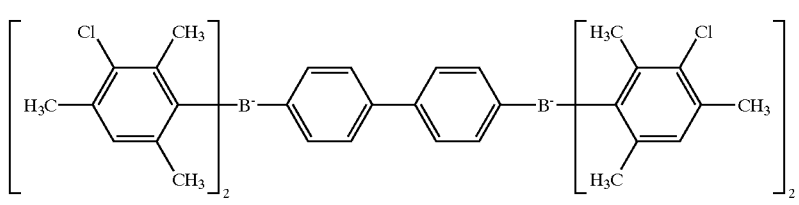

U.V. (CHCl$_3$) max. at 245 nm ($\epsilon$31900) and 305 nm ($\epsilon$41800).

$^1$H NMR (CDCl$_3$): 7.71–7.31 (20H, m, ArH), 6.86–6.57 (6H, m, ArH), 3.88 (2H, s, CH$_2$), 3.24 (2H, t, CH$_2$), 2.87 (2H, t, CH$_2$), 2.62 (2H, t, CH$_2$), 2.05 (12H, s, CH$_3$) and 2.4–1.5 (42H, m, CH$_2$ and CH$_3$).

Application Examples C
Process for UV-initiated Michael Addition with Dimethylmalonate and n-butylacrylate The latent base (7.4×10 mol) and 2,2,6,6-tetramethyl-1-piperidinyloxyl (7.4×10 mol) are dissolved in a 1:1 mixture of dimethylmalonate and n-butylacrylate (200 mg, 7.4×10$^{-4}$ mol).

This mixture is irradiated in a silica flask using a high-pressure mercury vapour lamp (200 watt) at a distance of 30 cm. After a certain time, the reaction is measured.

EXAMPLE C1

A compound of Example B13 is used. After a 2 hours exposure to light, a 55% reaction is found, and after 6 hours 100% are reacted.

EXAMPLE C2

A compound of Example B30 is used. Crosslinking is achieved by exposure to visible light.

Use Examples D

Base-catalysis with Oligomeric/Dolymeric Compounds

EXAMPLE D1

Preparation of Urethane Acrylate Based on Isophoronediisocyanate and 4-Hydroxybutylacrylate.

The reaction is carried out under nitrogen and all commercially available chemicals employed are used without further purification.

1566.8 g (13.78 mol NCO) of isophoronediisocyanate, 2.3 g of dibutyltin dilaurate, 2.3 g of 2,5-ditertiary-butyl-p-cresol and 802.8 g of butylacetate are placed in a three-necked flask equipped with condenser and dropping funnel. Dry nitrogen is made to bubble through the reaction mixture and the temperature is slowly raised to 60° C. Subsequently, 1987 g (13.78 mol) of 4-hydroxybutylacrylate are added, the reaction solution slowly heating to 80° C. The temperature is kept at 80° C. and the dropping funnel is rinsed with butylacetate (86.6 g). The reaction is observed via titration of the residual amount of isocyanate and is terminated when the isocyanate content is less than 0.2%, based on the solid. The reaction product obtained has the following physical properties:

Residual amount of 4-hydroxybutylacrylate: <0.002%, based on the solid (HPLC analysis),
colour: <<Gardner 1,
viscosity: 43 cPa s (20° C.), solid: 79.3% (1 hour at 140° C.),
GPC data (polystyrene standard), M$_n$ 778, M$_w$ 796, d=1.02.

Preparation of a Malonate Polyester

The reaction is carried out under nitrogen and all commercially available chemicals employed are used without further purification.

In a reaction vessel equipped with stirrer and condenser, 1045 g of 1.5 pentanediol, 1377.4 g of diethylmalonate and 242.1 g of xylene are carefully refluxed. The maximum temperature of the reaction mixture is 196° C. while the temperature is kept at 79° C. at the head of the condenser. 862 g of ethanol are thus isolated by distillation, corresponding to a 97.7% reaction. Xylene is then stripped off under vacuum at a temperature of 200° C. The polymer so obtained has 98.6% solid content, a viscosity of 2710 mmPa s and an acid number of 0.3 mg KOH/g, based on the solid. M$_n$ is 1838, M$_w$ is 3186, the colour is 175 on the APHA scale (process of the American Public Health Association; "Hazen colour unit"; ISO 6271).

Curing with UV Radiation 6.4·10$^{-5}$ Mol of the photoinitiator of Example B28 are dissolved in a 1:1 mixture of the above urethane acrylate and the malonate polyester (400 mg total amount). This mixture is cast on a glass plate to a 50 µm film and is irradiated using a high-pressure mercury vapour lamp (200 W) at a distance of 30 cm. The film is tack-free after 30 minutes.

What is claimed is:

1. A compound of formula (I)

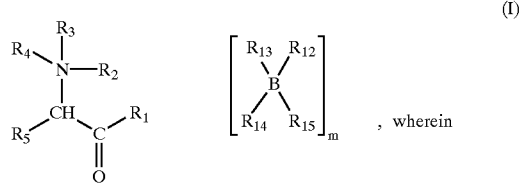

(I)

m is 1 or 2 and corresponds to the number of positive charges of the cation;

R$_1$ is phenyl, naphthyl, phenanthryl, anthracyl, pyrenyl, 5,6,7,8-tetrahydro-2-naphthyl, 5,6,7,8-tetrahydro-1-naphthyl, thienyl, benzo[b]thienyl, naphtho[2,3-b] thienyl, thianthrenyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, b-carbolinyl, phenanthridinyl, acridinyl, perimidinyl, phenanthrolinyl, phenazinyl, isothiazolyl, phenothiazinyl, isoxazolyl, furazanyl, terphenyl, stilbenyl, fluorenyl or phenoxazinyl, these radicals being unsubstituted or mono- or polysubstituted by $C_1$–$C_{18}$alkyl, $C_3$–$C_{18}$alkenyl, $C_3$–$C_{18}$alkynyl, $C_1$–$C_{18}$haloalkyl, $NO_2$, $NR_6R_7$, $N_3$, OH, CN, $OR_8$, $SR_8$, $C(O)R_9$, $C(O)OR_{10}$ or halogen, or $R_1$ is a radical of formula A or B

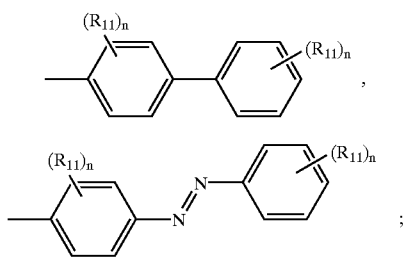 (A)

(B)

$R_2$, $R_3$ and $R_4$ are each independently of one another hydrogen, $C_1$–$C_{18}$alkyl, $C_3$–$C_{18}$alkenyl, $C_3$–$C_{18}$alkynyl or phenyl, or $R_2$ and $R_3$ and/or $R_4$ and $R_3$ form each independently of one another a $C_2$–$C_{12}$alkylene bridge; or $R_2$, $R_3$, $R_4$, together with the linking nitrogen atom, are a phosphazene base of the $P_1$, $P_2$, P <t/4> type or a group of the structural formula (a), (b), (c), (d), (e), (f) or (g)

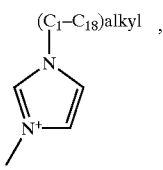 (a)

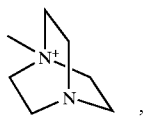 (b)

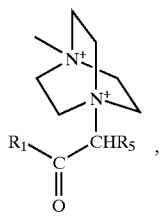 (c)

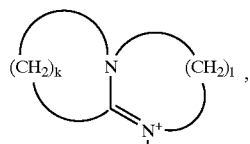 (d)

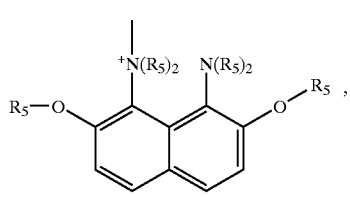 (e)

-continued

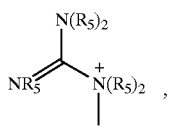 (f)

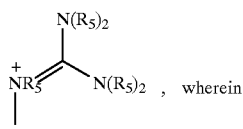 (g)

, wherein k and l are each independently of the other a number from 2 to 12;

$R_5$, $R_6$, $R_7$, $R_8$, $R_9$ and $R_{10}$ are hydrogen or $C_1$–$C_{18}$alkyl; or $R_5$ and $R_1$, together with the linking carbon atoms, are a benzocyclopentanone radical;

$R_{11}$, is $C_1$–$C_{18}$alkyl, $C_2$–$C_{18}$alkenyl, $C_2$–$C_{18}$alkynyl, $C_1$–$C_{18}$haloalkyl, $NO_2$, $NR_6R_7$, OH, CN, $OR_8$, $SR_8$, $C(O)R_9$, $C(O)OR_{10}$ or halogen; and n is 0 or 1, 2 or 3;

$R_{12}$, $R_{13}$ and $R_{14}$ is phenyl or another aromatic hydrocarbon, these radicals being unsubstituted or mono- or polysubstituted by $C_1$–$C_{18}$alkyl, $C_3$–$C_{18}$alkenyl, $C_3$–$C_{18}$alkynyl, $C_1$–$C_{18}$haloalkyl, $NO_2$, OH, CN, $OR_8$, $SR_8$, $C(O)R_9$, $C(O)OR_{10}$ or halogen;

$R_{15}$ is $C_1$–$C_{18}$alkyl, phenyl or another aromatic hydrocarbon, the radicals phenyl and aromatic hydrocarbon being unsubstituted or mono- or polysubstituted by $C_1$–$C_{18}$alkyl, $C_3$–$C_{18}$alkenyl, $C_3$–$C_{18}$alkynyl, $C_1$–$C_{18}$haloalkyl, $NO_2$, OH, CN, $OR_8$, $SR_8$, $C(O)R_9$, $C(O)OR_{10}$ or halogen, or $R_{15}$ is a radical

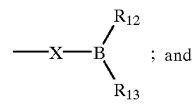 ; and

X is $C_1$–$C_{20}$alkylene, $C_2$–$C_{20}$alkylene which is interrupted by —O—, —S— or $NR_8$, or X is

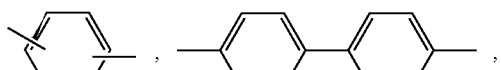

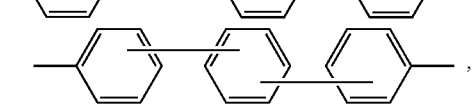

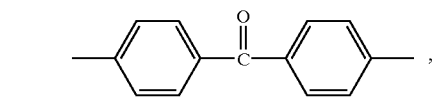

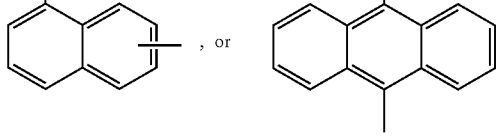

provided that, if $R_{12}$, $R_{13}$, $R_{14}$ and $R_{15}$ are each phenyl, $R_2$, $R_3$ and $R_4$ are not simultaneously methyl and $R_2$, $R_3$ and $R_4$ together with the linking nitrogen are not

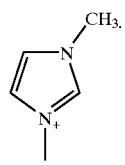

2. A compound according to claim 1, wherein $R_1$ is phenyl, naphthyl, pyrenyl, thioxanthyl or phenothiazinyl, which radicals are unsubstituted or mono- or polysubstituted by $C_1$–$C_{18}$alkyl, $C_1$–$C_{18}$haloalkyl, $NR_6R_7$, CN, $NO_2$, $SR_8$ or $OR_8$.

3. A compound according to claim 1, wherein $R_2$, $R_3$ and $R_4$ are each independently of one another hydrogen, $C_1$–$C_{18}$alkyl, or $R_2$ and $R_3$, and/or $R_4$ and $R_3$ form each independently of one another a $C_2$–$C_{12}$alkylene bridge; or $R_2$, $R_3$, $R_4$, together with the linking nitrogen, are a group of the structural formulae (a), (b), (c), (d), (e), (f), (g), (h) or a phosphazene base of the $P_1$, $P_2$ or P <t/4> type.

4. A compound according to claim 1, wherein $R_2$, $R_3$ and $R_4$ are each independently of one another $C_1$–$C_{18}$alkyl, or $R_2$, $R_3$, $R_4$, together with the nitrogen atom, are a group of the structural formula (a), (b), (c), (d) or (e).

5. A compound according to claim 1, wherein $R_{12}$, $R_{13}$, $R_{14}$ are phenyl, biphenyl, naphthyl, anthracyl or penanthryl, which radicals are unsubstituted or mono- or polysubstituted by $C_1$–$C_{18}$alkyl, $C_1$–$C_{18}$haloalkyl, $NO_2$, OH, CN, $OR_8$, or halogen, and $R_{15}$ is $C_1$–$C_{18}$alkyl or phenyl which is unsubstituted or mono- or polysubstituted by $C_1$–$C_{18}$alkyl, $C_1$–$C_{18}$haloalkyl, $NO_2$, OH, CN, $OR_8$ or halogen.

6. A process for the preparation of a compound of formula I according to claim 1, which comprises reacting in a first step a nitrogenous base of formula II

 (II)

with an α-halogen ketone of formula III

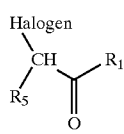 (III)

to a compound of formula IV

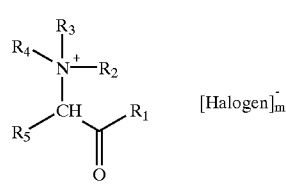 (IV)

and, in a second step, reacting the compound of formula IV with a compound of formula V

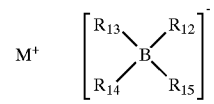 (V)

to the compound of formula 1, wherein halogen is bromo or iodo, and M is Na, K, or ammonium, and $R_1$, $R_2$, $R_3$, $R_4$, $R_5$, $R_{12}$, $R_{13}$, $R_{14}$ and $R_{15}$ have the meanings in claim 1.

7. A composition, which comprises

A) at least one compound of formula (I) according to claim 1, and

B) at least one organic compound which is capable of a base-catalysed addition reaction or substitution reaction.

8. A composition according to claim 7, wherein component B) is an anionically polymerisable or crosslinkable organic material.

9. A composition according to claim 7, wherein component B) is selected from one of the following systems:

a) an acrylate copolymer having alkoxysilane or alkoxysiloxane side groups, b) a two-component system comprising a hydroxyl group-containing polyacrylate and/or polyester and an aliphatic or aromatic polyisocyanate, c) a two-component system comprising a functional polyacrylate containing carboxyl or anhydride as functional groups and a polyepoxide, d) a two-component system comprising a fluorine-modified or silicone-modified hydroxyl group-containing polyacrylate or polyester and an aliphatic or aromatic polyisocyanate, e) a two-component system comprising a (poly)ketimine and an aliphatic or aromatic polyisocyanate, f) a two-component system comprising a (poly)ketimine and an unsaturated acrylate resin or an acetoacetate resin or methyl α-acrylamidomethylglycolate, h) a two-component system comprising a (poly) oxazolidine and a polyacrylate containing anhydride groups, or an unsaturated acrylate resin or a polyisocyanate, i) a two-component system comprising an epoxy group-containing polyacrylate and a carboxyl group-containing polyacrylate, l) a two-component system comprising a (poly)alcohol and a (poly)isocyanate, m) a two-component system comprising an α,β-ethylenically unsaturated carbonyl compound and a compound which contains activated $CH_2$ groups.

10. A composition according to claim 7, wherein component B) is selected from one of the following systems:

b) a two-component system comprising a hydroxyl group-containing polyacrylate and/or polyester and an aliphatic or aromatic polyisocyanate, c) a two-component system comprising a functional polyacrylate containing carboxyl or anhydride as functional groups and a polyepoxide, i) a two-component system comprising an epoxy group-containing polyacrylate and a carboxyl group-containing polyacrylate, m) a two-component system comprising a (poly)alcohol and a (poly)isocyanate, and n) a two-component system comprising an a,p-ethylenically unsaturated carbonyl compound and a compound which contains activated $CH_2$ groups.

11. A composition according to claim 7, wherein component B is an epoxy resin or a mixture of different epoxy resins.

12. A composition according to claim 7, wherein component A) is present in an amount of 0.01 to 10% by weight, based on component B).

13. A composition according to claim 7, which additionally comprises a sensitiser selected from the group consisting of thioxanthones, oxazines, acridines, phenazines and rhodamines.

14. A process for carrying out base-catalysed reactions, which comprises exposing a composition according to claim 7 with light having a wavelength in the range from 200 nm to 650 nm.

15. A process according to claim 14, which comprises heating the composition before or after the exposure to light.

16. A process according to claim 14 for the preparation of coatings, moulding compositions or photostructured layers.

17. A coated substrate, which is coated on at least one surface with a composition as claimed in claim 7.

18. A polymerised or crosslinked composition according to claim 7.

* * * * *